United States Patent
Matsuura et al.

(10) Patent No.: US 8,575,314 B2
(45) Date of Patent: Nov. 5, 2013

(54) ANTIBODY AGAINST OXIDIZED LDL/$\beta_2$GPI COMPLEX AND USE OF THE SAME

(75) Inventors: Eiji Matsuura, Okayama (JP); Kazuo Kojima, Nagano (JP)

(73) Assignees: National University Corporation Okayama University (JP); Medical and Biological Laboratories Co., Ltd. (JP)

(*) Notice: Subject to any disclaimer, the term of this patent is extended or adjusted under 35 U.S.C. 154(b) by 67 days.

(21) Appl. No.: 13/000,319

(22) PCT Filed: Mar. 9, 2009

(86) PCT No.: PCT/JP2009/054473
§ 371 (c)(1),
(2), (4) Date: Apr. 4, 2011

(87) PCT Pub. No.: WO2009/154025
PCT Pub. Date: Dec. 23, 2009

(65) Prior Publication Data
US 2011/0182816 A1    Jul. 28, 2011

(30) Foreign Application Priority Data

Jun. 20, 2008 (JP) ................................. 2008-162565

(51) Int. Cl.
| C07K 16/00 | (2006.01) |
| C12P 21/08 | (2006.01) |
| A61K 49/00 | (2006.01) |

(52) U.S. Cl.
USPC ....................... 530/387.1; 530/387.3; 424/9.1

(58) Field of Classification Search
None
See application file for complete search history.

(56) References Cited

U.S. PATENT DOCUMENTS

| 5,223,409 A | 6/1993 | Ladner et al. |
| 5,403,484 A | 4/1995 | Ladner et al. |
| 5,427,908 A | 6/1995 | Dower et al. |
| 5,432,018 A | 7/1995 | Dower et al. |
| 5,498,530 A | 3/1996 | Schatz et al. |
| 5,498,538 A | 3/1996 | Kay et al. |
| 5,571,689 A | 11/1996 | Heuckeroth et al. |
| 5,580,717 A | 12/1996 | Dower et al. |
| 5,585,089 A | 12/1996 | Queen et al. |
| 5,627,024 A | 5/1997 | Maruyama et al. |
| 5,663,143 A | 9/1997 | Ley et al. |
| 5,693,761 A | 12/1997 | Queen et al. |
| 5,693,762 A | 12/1997 | Queen et al. |
| 5,698,426 A | 12/1997 | Huse |
| 5,723,286 A | 3/1998 | Dower et al. |
| 5,723,323 A | 3/1998 | Kauffman et al. |
| 5,734,018 A | 3/1998 | Rutter et al. |
| 5,763,192 A | 6/1998 | Kauffman et al. |
| 5,766,905 A | 6/1998 | Studier et al. |
| 5,770,434 A | 6/1998 | Huse |
| 5,900,359 A | 5/1999 | Matsuura et al. |
| 6,180,370 B1 | 1/2001 | Queen et al. |
| 6,375,925 B1 | 4/2002 | Tsimikas et al. |
| 6,716,410 B1 | 4/2004 | Witztum et al. |
| 7,160,733 B2 | 1/2007 | Matsuura et al. |
| 7,455,976 B2 | 11/2008 | Matsuura et al. |
| 2004/0241858 A1 | 12/2004 | Matsuura et al. |
| 2006/0099644 A1 | 5/2006 | Matsuura |
| 2006/0194270 A1 | 8/2006 | Matsuura |
| 2008/0160018 A1 | 7/2008 | Queen et al. |
| 2010/0081149 A1 | 4/2010 | Matsuura et al. |
| 2011/0182817 A1 | 7/2011 | Matsuura et al. |

FOREIGN PATENT DOCUMENTS

| EP | 0682040 A1 | 11/1995 |
| EP | 0451216 B1 | 1/1996 |
| EP | 0722086 A1 | 7/1996 |
| EP | 1548436 A1 | 6/2005 |
| JP | 01-59878 B | 12/1989 |
| JP | 07-238098 A | 9/1995 |
| JP | 2828340 B2 | 11/1998 |
| JP | 2001-506983 A | 5/2001 |
| JP | 3370334 B2 | 1/2003 |
| JP | 2004-271502 A | 9/2004 |
| JP | 3898680 B2 | 3/2007 |
| JP | 4044972 B2 | 2/2008 |
| WO | WO-83/04313 A1 | 12/1983 |
| WO | WO-92/01047 A1 | 1/1992 |
| WO | WO-92/03918 A1 | 3/1992 |
| WO | WO-92/20791 A1 | 11/1992 |
| WO | WO-93/06213 A1 | 4/1993 |
| WO | WO-93/11236 A1 | 6/1993 |
| WO | WO-93/12227 A1 | 6/1993 |
| WO | WO-93/19172 A1 | 9/1993 |
| WO | WO-94/02602 A1 | 2/1994 |
| WO | WO-94/25585 A1 | 11/1994 |
| WO | WO-95/01438 A1 | 1/1995 |
| WO | WO-95/09363 A1 | 4/1995 |

(Continued)

OTHER PUBLICATIONS

MacCallum et al (1996. Journal of Molecular Biology. 262: 732-745).*
Pascalis et al (2002. Journal of Immunology. 169:3076-3084).*
Casset et al (2003. Biochemical and Biophysical Research Communications. 307: 198-205).*
Vajdos et al (2002. Journal of Molecular biology. 320: 415-428),.*
Holm et al (2007. Molecular Immunology. 44: 1075-1084).*
Chen et al (1999. Journal of Molecular Biology. 293: 865-881).*
Wu et al (1999. Journal of Molecular Biology. 294: 151-162).*
"International Application Serial No. PCT/JP2009/054473, International Preliminary Report on Patentability mailed Mar. 17, 2011", (English Translation), 6 pgs.
"International Application Serial No. PCT/JP2009/054473, International Search Report mailed Apr. 7, 2009", (w/ English Translation), 4 pgs.

(Continued)

Primary Examiner — Zachary Howard
(74) Attorney, Agent, or Firm — Schwegman, Lundberg & Woessner, P.A.

(57) ABSTRACT

From antibodies that can be used to immunostain atherosclerotic tissue sections, the present inventors selected antibodies applicable to in vivo imaging, and analyzed their specificities. The result showed that fluorescently labeled anti-oxidized LDL/$\beta_2$GPI complex antibodies that are specific to a particular epitope were effective for imaging.

11 Claims, 11 Drawing Sheets

(56) References Cited

FOREIGN PATENT DOCUMENTS

| WO | WO-95/15388 A1 | 6/1995 |
|---|---|---|
| WO | WO-95/34683 A1 | 12/1995 |
| WO | WO-96/33735 A1 | 10/1996 |
| WO | WO-96/34096 A1 | 10/1996 |
| WO | WO-97/09446 A1 | 3/1997 |
| WO | WO-97/35196 A1 | 9/1997 |
| WO | WO-97/46251 A1 | 12/1997 |
| WO | WO-97/47314 A1 | 12/1997 |
| WO | WO-98/14277 A1 | 4/1998 |
| WO | WO-98/15833 A1 | 4/1998 |
| WO | WO-98/20036 A1 | 5/1998 |
| WO | WO-98/20159 A1 | 5/1998 |
| WO | WO-98/20169 A1 | 5/1998 |
| WO | WO-98/23282 A1 | 6/1998 |
| WO | WO-03/022866 A1 | 3/2003 |
| WO | WO-2004/023141 A1 | 3/2004 |
| WO | WO-2007/139099 A1 | 12/2007 |

OTHER PUBLICATIONS

Machine Translation of JP 4044972B2, published Feb. 6, 2008, 13 pgs.
Itabe, H., et al., "A Monoclonal Antibody against Oxidized Lipoprotein Recognizes Foam Cells in Atherosclerotic Lesions", *The Journal of Biological Chemistry*, 269(21), (1994), 15274-15279.
Kobayashi, K., et al., "Circulating oxidized LDL forms complexes with Beta2-glycoprotein I: implication as an atherogenic autoantigen", *Journal of Lipid Research*, 44, (2003), 716-726.
Lanza, G. M., et al., "Molecular Imaging and Therapy: New Paradigms for 21st Century Medicine", *American Chemical Society Symposium Series*, 923, (2006), 295-311.
Matsuura, E., et al., "Establishing the Innovative Diagnostic Imaging Method for Arteriosclerosis", Report of the Results of 2007 MHLW Research Grant Program—Discovery of Nanobio-targeted Theraphy and Other Innovative Therapies and Researches onthe Underlying Technologies, (w/ English Translation), (Mar. 2008), 19-28.
Matsuura, E., "Establishing the Innovative Diagnostic Imaging Method for Arteriosclerosis", 2007 MHLW Science and Technology Promotion Program for the Prefectures Where Special Electric Generation Plants are Located—Discovery of Nanobio-targeted Therapy and Other Innovative Therapies and Researches on the Underlying Technologies, (w/ English Translation), (2008), 12 pgs.
Matsuura, E., et al., "Ko-rin Shishitsu Kotai Shokogun no Shindanho: Sanka LDL $\beta_2$-glycoprotein I Fukugotai Jiko Kogen) to scrrera no Men'eki Fukugotai no Sokutei Igi", Kosei Kagaku Kenkyuhi Hojokin (Tokutei Shikkan Taisaku Kenkyu Jigyo), Jiko Men'eki Shikkan ni Kansuru Chosa Kenkyu Heisei 14 Nendo Sokatsu—Buntan Kenkyu Hokoku, (2003), 93-97.
Matsuura, E., et al., "Sanka LDL $\beta_2$-glycoprotein I Fukugotai to Domyaku Kokasei Shikkan Jiko Kotai to Jiko Men'eki '06", Dai 13 Kai Jiko Kotai to Jiko Men'eki Symposium Koen Rokushu, (Aug. 25, 2006), 19-25.
Matsuura, E., et al., "Establishing the Innovative Diagnostic Imaging Method for Arteriosclerosis [Kakkiteki na Domyaku Koka no Gazo Shindanho no Kakuritsu]", *2007 MHLW Science and Technology Promotion Program for the Prefectures Where Special Electric Generation Plants are Located, Discovery of Nanobio-targeted Therapy and Other Innovative Therapies and Researches on the Underlying Technologies—A Conference to Report Research Outcomes* (w/ English Translation), (Mar. 11, 2008), 12 pgs.
European Application Serial No. 09766473.4, Supplementary European Search Report mailed Oct. 15, 2012, 6 pgs.
Rudikoff, S., et al., "Single amino acid substitution altering antigen-binding specificity", *Proc. Natl. Acad. Sci. USA*, 79, (Mar. 1982), 1979-1983.
Tabuchi, M., et al., "The association of C-reactive protein with an oxidative metabolite of LDL and its implication in atherosclerosis", *Journal of Lipid Research*, 48, (2007), 768-781.

\* cited by examiner

HEAVY CHAIN (SEQ ID NO: 1)

```
         10         20         30         40         50         60
EVQLVESGGG LVKPGGSLKL SCAASGFTFS SYAMSWARQT PEKRLEWVAT ISSGGSYTYY
                                     CDR1                CDR2
         70         80         90        100        110
PDSVRGRFTI SRDNAKNTLY LQMCSLRSED TAMYYCARED GYYAMDYWGQ GTSVTVSS
                                          CDR3
```

LIGHT CHAIN (SEQ ID NO: 6)

```
         10         20         30         40         50         60
DIVMTQSHKF MSTSVGDRVS ITCKASQDVG SAVAWYQQKP GQSPKLLIYW ASTRHTGVPD
                         CDR1                           CDR2
         70         80         90        100        110
RFTGSGSGTD FTLTISSLQS EDLADYFCQQ YSSYPLTFGS GTKLEIK
                                 CDR3
```

FIG. 11

ANTIBODY AGAINST OXIDIZED LDL/β₂GPI COMPLEX AND USE OF THE SAME

RELATED APPLICATION

This application is a nationalization under 35 U.S.C. 371 of PCT/JP2009/054473, filed Mar. 9, 2009 and published as WO 2009/154025 A1 on Dec. 23, 2009, which claimed priority under 35 U.S.C. 119 to Japanese Patent Application No. 2008-162565, filed Jun. 20, 2008; which applications and publication are incorporated herein by reference in their entirety.

TECHNICAL FIELD

The present invention relates to antibodies against an oxidized LDL/β₂GPI complex, and non-invasive diagnostic methods for arteriosclerosis using the antibodies such as methods for identifying atherosclerotic lesion sites and methods for monitoring the therapeutic effects.

BACKGROUND ART

Diagnostic methods for assessing the condition of arteriosclerosis, which have already been put to practical use, include, for example, the four methods described below.

"Ankle-brachial pressure index": When blood pressure is measured at the arm and ankle levels in the supine position, the ankle blood pressure is normally slightly higher. However, the narrowing of a blood vessel reduces the downstream blood pressure, which results in a decrease in the ratio of ankle blood pressure to brachial blood pressure (ABI). A decrease in ABI not only indicates arteriosclerosis in the artery of the lower limb but also suggests systemic arteriosclerosis.

"Pulse wave velocity test": A method for estimating the progression of arteriosclerosis by assessing arterial stiffness. In healthy individuals, blood vessels are elastic and thus vascular walls absorb vibration, resulting in a reduction in pulse wave velocity. As arteriosclerosis advances, the wave velocity increases. Thus, the progression of arteriosclerosis can be estimated using the velocity as an indicator.

"Carotid ultrasound examination": A method for estimating the progression of systemic arteriosclerosis by observing carotid arteries which run very close to the surface of skin and have an interior condition that is easy to observe by ultrasound.

"MR angiography (MRA)" and "CT angiography (CTA)": Angiography was used as a major diagnostic imaging method for vascular diseases, but image information that is almost comparable to angiography but obtained in a less invasive manner has become available. The advantages of CTA include: (1) high spatial resolution; (2) simple examination; and (3) superiority in detecting calcified lesions.

The above-described "ankle-brachial pressure index" and "pulse wave velocity test" can neither identify the site of atherosclerosis nor diagnose the progression at each site. Thus, these methods only provide indirect scores to assess arteriosclerosis.

Unlike pulse wave velocity test or such, "carotid ultrasound examination" is superior in that it enables direct graphical observation of the inside of blood vessels. However, the condition of vascular wall is assessed based on the contrasting density and shape in ultrasonic images, and thus clinicians and laboratory technicians who conduct the test are required to have skills. Furthermore, the test cannot identify the site of atherosclerosis or diagnose the progression at individual sites in blood vessels other than the carotid artery.

Meanwhile, methods for monitoring the progression of arteriosclerosis include ELISA systems for measuring the oxidized LDL/β₂GPI complex in blood (Japanese Patent Nos. 3370334 and 3898680; WO2003/022866, WO2004/023141). However, conventional ELISA for measuring the oxidized LDL/β₂GPI complex can be used to estimate the size but not the site of atherosclerotic plaque.

Meanwhile, even when MRI or radiolabeled imaging is used, the condition of vascular wall is assessed based on the contrasting densities and shapes in ultrasonic images, and thus clinicians and laboratory technicians who conduct the test are required to have skills and expertise (U.S. Pat. Nos. 6,716,410 and 6,375,925).

Prior art documents related to the present invention include:
[Patent Document 1] Japanese Patent No. 3370334
[Patent Document 2] Japanese Patent No. 3898680
[Patent Document 3] WO 2003/022866
[Patent Document 4] WO 2004/023141
[Patent Document 5] Japanese Patent Application Kohyo Publication No. (JP-A) 2001-506983 (unexamined Japanese national phase publication corresponding to a non-Japanese international publication)
[Patent Document 6] Japanese Patent No. 4044972
[Patent Document 7] U.S. Pat. No. 6,716,410
[Patent Document 8] U.S. Pat. No. 6,375,925
[Non-patent Document 1] Journal of Biological Chemistry 269, 15274-15279, 1994

DISCLOSURE OF THE INVENTION

Problems to be Solved by the Invention

An objective of the present invention is to provide antibodies against an oxidized LDL/β₂GPI complex, and non-invasive diagnostic methods for arteriosclerosis using the antibodies such as methods for identifying arteriosclerosis lesion sites and methods for monitoring the therapeutic effects.

Means for Solving the Problems

From antibodies that can be used to immunostain atherosclerotic tissue sections, the present inventors selected antibodies applicable to in vivo imaging, specifically to visualize atherosclerotic plaques, in particular, the location and size of atheroma in the body. Then, the prevent inventors analyzed the specificities of the antibodies. The result showed that fluorescently labeled anti-oxidized LDL/β₂GPI complex antibodies that are specific to a particular epitope were effective for imaging.

Specifically, the present invention provides:
[1] an antibody of any one of (a) to (e) below, which binds to a complex of oxidized LDL and β₂-glycoprotein I (oxidized LDL/β₂GPI complex):
 (a) an antibody comprising a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4;
 (b) an antibody comprising a heavy chain that comprises a heavy-chain variable region having the amino acid sequence of SEQ ID NO: 1;
 (c) an antibody comprising a light chain that comprises CDR1 having the amino acid sequence of SEQ ID NO: 7, CDR2 having the amino acid sequence of SEQ ID NO: 8, and CDR3 having the amino acid sequence of SEQ ID NO: 9;

(d) an antibody comprising a light chain that comprises a light-chain variable region having the amino acid sequence of SEQ ID NO: 6; and (e) an antibody that comprises a pair of the heavy chain of (a) or (b) above and the light chain of (c) or (d) above;
[2] an antibody that binds to the same epitope as the antibody of any one of [1];
[3] the antibody of [1] or [2], which is a humanized or chimeric antibody;
[4] an imaging agent for visualizing an arteriosclerosis site, which comprises an antibody that binds to a complex of oxidized LDL and $\beta_2$-glycoprotein I (oxidized LDL/$\beta_2$GPI complex);
[5] an imaging agent for visualizing an arteriosclerosis site, which comprises the antibody of any one of [1] to [3];
[6] the imaging agent of [4] or [5], for determining the location and/or size of atheroma in arteriosclerosis;
[7] an imaging kit for visualizing an arteriosclerosis site, which comprises an antibody that binds to a complex of oxidized LDL and $\beta_2$-glycoprotein I (oxidized LDL/$\beta_2$GPI complex);
[8] an imaging kit for visualizing an arteriosclerosis site, which comprises the antibody of any one of [1] to [3];
[9] a method of screening for a candidate compound for a therapeutic agent for arteriosclerosis, which comprises the steps of:

(a) administering a candidate compound to an arteriosclerosis model nonhuman animal administered with the antibody of any one of [1] to [3];

(b) carrying out imaging of an arteriosclerotic plaque in an arteriosclerosis model nonhuman animal administered with the candidate compound and in an arteriosclerosis model nonhuman animal not administered with the candidate compound;

(c) comparing the size or location of an arteriosclerotic plaque between the arteriosclerosis model nonhuman animal administered with the candidate compound and the arteriosclerosis model nonhuman animal not administered with the candidate compound; and (d) selecting a candidate compound that reduces or eliminates an arteriosclerotic plaque in the arteriosclerosis model nonhuman animal administered with the candidate compound as compared to the arteriosclerosis model nonhuman animal not administered with the candidate compound;
[10] an imaging agent for visualizing an arteriosclerosis site, which comprises the antibody of any one of [1] to [3];
[11] use of the antibody of any one of [1] to [3] for the manufacture of an imaging agent for visualizing an arteriosclerosis site; and
[12] the antibody of any one of [1] to [3] for use in an imaging method for visualizing an arteriosclerosis site.

BRIEF DESCRIPTION OF THE DRAWINGS

FIG. 11 is a diagram showing the amino acid sequence of antibody 3H3. Each CDR is underlined.

MODE FOR CARRYING OUT THE INVENTION

Figure 1:
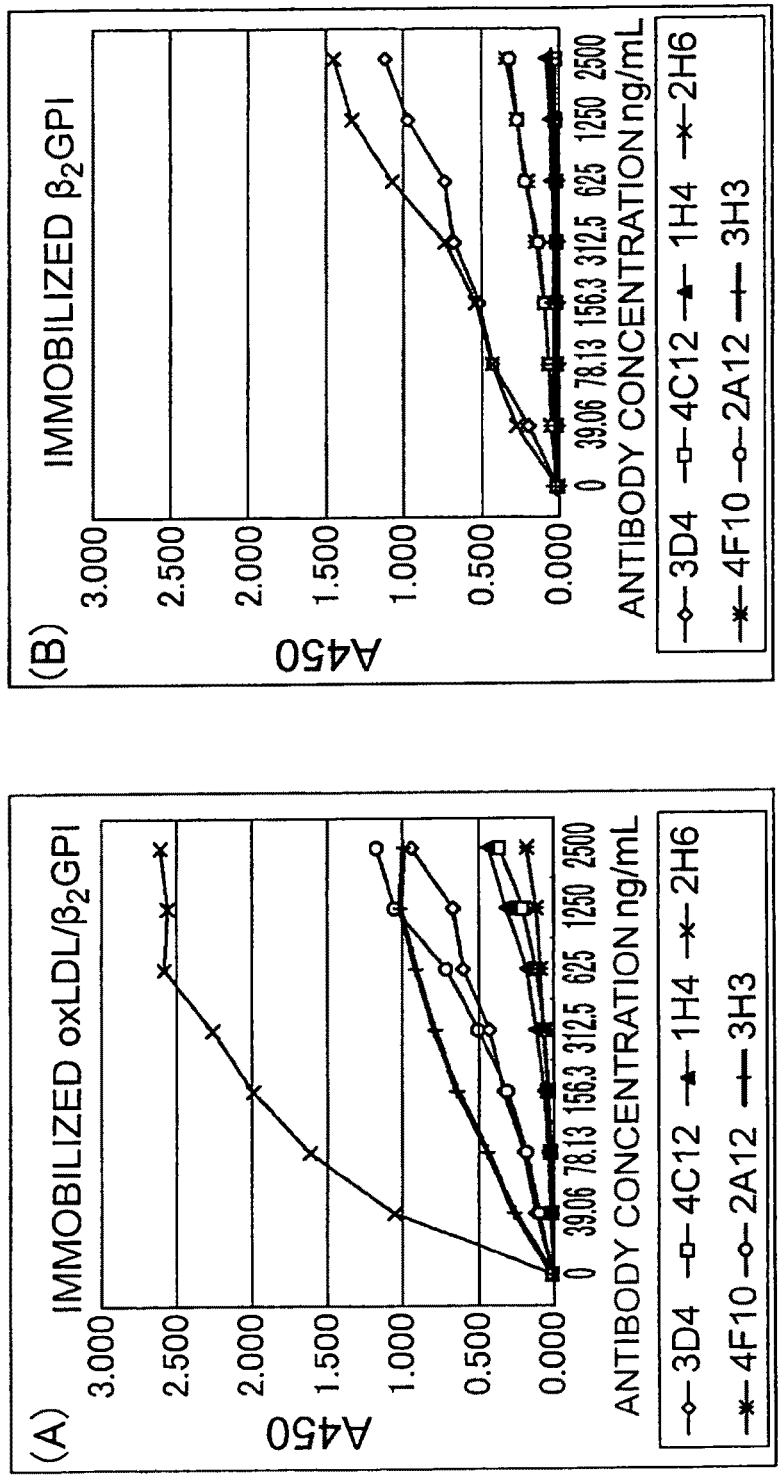
FIGS. 1A-B are diagrams showing antibody reactivities to immobilized antigen. The antibodies were monoclonal antibodies obtained by immunizing BALB/c mice with the oxidized LDL/$\beta_2$GPI complex as an antigen. The horizontal axis indicates antibody concentration, and the vertical axis indicates the absorbance.

The present invention provides antibodies that bind to a complex of oxidatively modified LDL (oxidized LDL) and β$_2$-glycoprotein I (oxidized LDL/β$_2$GPI complex). The complex is formed between oxidized LDL and β$_2$GP in atherosclerotic plaques. β$_2$GP is a serum glycoprotein. The antibodies of the present invention bind to the complex.

Specifically, the antibodies of the present invention include those described below, but are not limited thereto:

(a) an antibody comprising a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4;

(b) an antibody comprising a heavy chain that comprises a heavy-chain variable region having the amino acid sequence of SEQ ID NO: 1;

(c) an antibody comprising a light chain that comprises CDR1 having the amino acid sequence of SEQ ID NO: 7, CDR2 having the amino acid sequence of SEQ ID NO: 8, and CDR3 having the amino acid sequence of SEQ ID NO: 9;

(d) an antibody comprising a light chain that comprises a light-chain variable region having the amino acid sequence of SEQ ID NO: 6; and (e) an antibody comprising a pair of the heavy chain of (a) or (b) above and the light chain (c) or (d) above.

The present invention also provides antibodies that bind to the same epitope as an antibody of the present invention that binds to the complex of oxidized LDL and β$_2$-glycoprotein I (oxidized LDL/β$_2$GPI complex). Such antibodies recognize a particular epitope on the oxidized LDL/β$_2$GPI molecule which is a complex formed with oxidized LDL.

Whether an antibody recognizes the same epitope as another antibody can be confirmed, for example, by their competition for the epitope, although the test method is not limited thereto. The competition between antibodies can be assessed by competitive binding assays. The method includes ELISA, fluorescence resonance energy transfer (FRET), and fluorometric microvolume assay technology (FMAT™). The amount of a particular antibody bound to antigen is indirectly correlated with the binding activity of a competitor antibody candidate (test antibody), which competes for the binding to the same epitope. Specifically, as the amount or affinity of a test antibody for the same epitope increases, the amount of an antibody bound to the antigen decreases, and the amount of test antibody bound to the antigen increases. More specifically, an appropriately labeled antibody is added to the antigen together with a test antibody, and then the bound antibody is detected using the label. The amount of an antibody bound to the antigen can be readily determined by labeling the antibody in advance. Such labels are not particularly limited; however, appropriate labeling methods are selected depending on the technique. Such labeling methods include, for example, fluorescent labeling, radiolabeling, and enzyme labeling.

Herein, "antibody that recognizes the same epitope" refers to an antibody that can reduce the amount of labeled antibody bound by at least 50%, when a test antibody is used at a concentration typically 100 times higher, preferably 80 times higher, more preferably 50 times higher, even preferably 30 times higher, and still preferably 10 times higher than the IC$_{50}$ of the non-labeled antibody, where IC$_{50}$ is defined as a concentration of a non-labeled antibody at which the amount of the labeled antibody bound is decreased by 50% due to the binding of the non-labeled antibody.

The antibodies of the present invention include both polyclonal and monoclonal antibodies. Methods for preparing and purifying monoclonal and polyclonal antibodies are known in the field, and described, for example, in "Harlow and Lane, Antibodies: A Laboratory Manual (New York: Cold Spring Harbor Laboratory Press, 1988)".

The antibodies of the present invention also include recombinant antibodies such as humanized antibodies and chimeric antibodies. "Humanized antibody" refers to an antibody whose structure is similar to that of a human antibody. Such humanized antibodies and chimeric antibodies include human-type chimeric antibodies (for example, antibodies in which some portions have been humanized, antibodies whose CH2 region has been humanized, antibodies whose Fc domain has been humanized, antibodies whose constant region has been humanized), CDR-grafted humanized antibodies whose constant and variable regions have been humanized except their complementarity determining regions (CDRs) (P. T. Johons et al., Nature 321, 522 (1986)), and completely humanized antibodies. Improvement methods for enhancing the antigen binding activity of a CDR-grafted human-type antibody have been developed, which include: methods for selecting human antibody FRs that are highly homologous to the mouse antibody, methods for producing highly homologous humanized antibodies, and methods for substituting amino acids in FR after grafting mouse CDRs to human antibodies (see U.S. Pat. Nos. 5,585,089, 5,693,761, 5,693,762, and 6180370; EP Nos. 451216 and 682040; Japanese Patent No. 2828340). Such methods can be used to prepare CDR-grafted human-type antibodies of the present invention.

Human-type chimeric antibodies can be produced, for example, by substituting a human anybody constant region for the constant region of an above-described antibody having the structure of an H-chain variable region and/or the structure of an L-chain variable region described above. Such human antibody constant regions include known human antibody constant regions. A method for producing human-type chimeric antibodies is described below as an example.

First, mRNA is extracted from hybridomas producing a mouse antibody against a particular target antigen. cDNA is synthesized from the mRNA by a conventional method. The synthesized cDNA is inserted into a vector to construct a cDNA library. A vector carrying H-chain and L-chain genes is selected from the cDNA library using H-chain gene and L-chain gene fragments as a probe. The sequences of the H-chain variable region and L-chain variable region genes are determined by sequencing the insert in the selected vector. DNA encoding the H-chain variable region is constructed based on the sequence data obtained as described above by chemical synthesis, biochemical cleavage/ligation, or the like. The resulting DNA that encodes the H-chain variable region is ligated with a DNA encoding human H-chain constant region, and then inserted into an expression vector to construct an expression vector for H chain. Such expression vectors include, for example, SV40 virus-based vectors, EB virus-based vectors, and papilloma virus (BPV)-based vectors, but are not limited thereto. Furthermore, expression vectors for L chain are constructed by the same method. Host cells are co-transformed with the H-chain expression vectors and L-chain expression vectors. Preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prev. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Feigner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type chimeric antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

Meanwhile, human-type CDR-grafted antibodies can be produced, for example, by the following method. First, the amino acid sequences of H-chain and L-chain variable regions of an antibody against a particular antigen, and nucleotide sequences encoding them are determined by the methods for producing chimeric antibodies as described above. The amino acid and nucleotide sequences of each CDR are determined as well.

Next, framework regions (FRs) which sandwich CDRs are selected. Three methods are available for selecting FRs. The first method uses human antibody frames with known three dimensional structures, such as NEWM and REI (Riechmann L. et al., Nature 332, 323-3Z7 (1988); Tempst, P R. et al., Protein Engineering 7, 1501-1507 (1994); Ellis J H. et al., J. Immunol 155, 925-937 (1995)). The second method uses FRs of a human antibody variable region that is most homologous to a mouse antibody variable region of interest, in which the human antibody variable region is selected from databases (Queen C. et al., Proc Natl Acad Sci USA 86, 10029-10033 (1989); Rozak M J. et al., J Biol Chem 271, 22611-22618 (1996); Shearman C W. et al., J. Immunol 147, 4366-4373 (1991)). In the third method, amino acids most commonly shared by human antibody FRs are selected (Sato K. et al., Mol Immunol 31, 371-381 (1994); Kobinger F. et al., Protein Engineering 6, 971-980 (1993); Kettleborough C A. et al., Protein Engineering 4, 773-783 (1991)). All of these methods can be used in the present invention.

Furthermore, FR amino acid sequences to be used also include amino acid sequences resulting from modification of the amino acid sequence of a selected human FR, as long as the human-type CDR-grafted antibody produced from it has the activity of specifically binding to the target antigen. In particular, when a portion of the amino acid sequence of a selected human FR is replaced with the amino acid sequence of an FR of the antibody from which CDR is derived, the resulting antibody is very likely to retain the antibody properties. The number of amino acids to be modified is preferably 30% or less in a whole FR, more preferably 20% or less in a whole FR, and still more preferably 10% or less in a whole FR.

Next, DNAs encoding H-chain and L-chain variable regions are designed by combining the above-described CDRs with FRs selected by any one of the methods described above. Based on this design, DNAs encoding H-chain variable regions and DNAs encoding L-chain variable regions are prepared by chemical synthesis, biochemical cleavage/ligation, or the like. Then, an H-chain expression vector is constructed by inserting into an expression vector the H-chain variable region-encoding DNA, along with a DNA encoding an H-chain constant region of human immunoglobulin. Likewise, an L-chain expression vector is constructed by inserting into an expression vector the L-chain variable region-encoding DNA, along with a DNA encoding an L-chain constant region of human immunoglobulin. Expression vectors include, for example, SV40 virus-based vectors, EB virus-based vectors, and papilloma virus (BPV)-based vectors, but are not limited thereto.

Host cells are co-transformed with the H-chain expression vectors and L-chain expression vectors prepared by the method described above. Such preferred host cells include CHO cells (Chinese hamster ovary) (A. Wright & S. L. Morrison, J. Immunol. 160, 3393-3402 (1998)) and SP2/0 cells (mouse myeloma) (K. Motmans et al., Eur. J. Cancer Prev. 5, 512-519 (1996); R. P. Junghans et al., Cancer Res. 50, 1495-1502 (1990)). Transformation can be preferably carried out by using electroporation, a lipofectin method (R. W. Malone et al., Proc. Natl. Acad. Sci. USA 86, 6077 (1989); P. L. Feigner et al., Proc. Natl. Acad. Sci. USA 84, 7413 (1987)), calcium phosphate method (F. L. Graham & A. J. van der Eb, Virology 52, 456-467 (1973)), DEAE-Dextran method, and the like.

The transformants are cultured, and then human-type CDR-grafted antibodies are isolated from the transformants or culture media. Antibodies can be isolated or purified by an appropriate combination of methods such as centrifugation, ammonium sulfate fractionation, salting out, ultrafiltration, affinity chromatography, ion exchange chromatography, and gel filtration chromatography.

Methods for preparing human antibodies are also known. For example, desired human antibodies with antigen-binding activity can be obtained by sensitizing human lymphocytes in vitro with an antigen of interest or cells expressing an antigen of interest; and fusing the sensitized lymphocytes with human myeloma cells such as U266 (see Japanese Patent Application Kokoku Publication No. (JP-B) H01-59878 (examined, approved Japanese patent application published for opposition)). Alternatively, desired human antibodies can also be obtained by using an antigen of interest to immunize transgenic animals that have the entire repertoire of human antibody genes (see International Patent Application WO 93/12227, WO 92/03918, WO 94/02602, WO 94/25585, WO 96/34096, and WO 96/33735).

In an alternative embodiment, antibodies and antibody fragments can be isolated from an antibody phage library produced by using the technique described by McCafferty et al. (Nature, 348: 552-554 (1990)). Clackson et al. (Nature, 352: 624-628 (1991)) and Marks et al. (J. Mol. Biol., 222: 581-597 (1991)) reported isolation of mouse and human antibodies using phage libraries. Subsequently published documents describe generation of high-affinity (nM range) human antibodies by chain shuffling (Marks et al., Bio/Technology, 10: 779-783 (1992)); and combinatorial infection and in vivo recombination as a strategy for constructing very large phage libraries (Waterhouse et al., Nuc. Acids. Res., 21: 2265-2266 (1993)). These techniques can serve as an alternative method for isolating monoclonal antibodies, which are used instead of the conventional hybridoma method for preparing monoclonal antibodies.

In this context, the bacteriophage (phage) display is one of the well-known techniques that enable one to search a large oligopeptide library and identify library members having the ability to specifically bind to a target polypeptide. The phage display is a technique that displays various polypeptides as a fusion protein with the coat protein on the surface of bacteriophage particles (Scott, J. K. and Smith G. P. Science 249: 386 (1990)). An advantage of phage display is that it enables rapid and effective categorization of a large library of selectively randomized protein mutants (or random cDNA clones) for the sequences that bind with high affinity to a target molecule. The phage display of peptide library (Cwirla, S. E. et al., Proc. Natl. Acad. Sci. USA, 87: 6378 (1990)) or protein library (Lowman, H. B. et al., Biochemistry, 30: 10832 (1991); Clackson, T. et al., Nature, 352:624 (1991); Marks, J. D. et al., J. Mol. Biol., 222: 581 (1991); Kang, A. S. et al., Proc. Natl. Acad. Sci. USA, 88:8363 (1991)) has been used to screen a vast number of oligopeptides or polypeptides for those that have a specific binding property (Smith, G P. Current Opin. Biotechnol., 2:668 (1991)). Categorization in a phage library of random mutants requires a method for constructing and propagating a vast number of mutants; an affinity purification method using a target receptor; and a method for assessing the enhanced binding (see U.S. Pat. Nos. 5,223, 409, 5,403,484, 5,571,689, and 5663143).

Most phage display methods use filamentous phages; however, known phage display methods also include λ phage display system (WO 95/34683; U.S. Pat. No. 5,627,024), T4 phage display system (Ren J. et al., Gene 215: 439 (1998); Zhu et al., Cancer Research, 58 (15):3209-3214 (1998); Jiang et al., Infection & Immunity, 65(11): 4770-4777 (1997); Ren et al., Gene, 195(2): 303-311 (1997); Ren, Protein Sci. 5: 1833 (1996); Efimov et al., Virus Genes 10: 173 (1995)) and T7 phage display system (Smith and Scott, Methods in Enzymology, 217, 228-257 (1993); U.S. Pat. No. 5,766,905).

To date, there are many improved and modified methods developed based on the basic phage display method. These modifications have improved the methods for screening peptide or protein libraries based on a property or ability such as the activity of binding to a selected target molecule. Recombination means for the phage display method are described in WO 98/14277. Phage display libraries have been used to analyze and control bimolecular interactions (WO 98/20169; WO 98/20159) and properties of constrained helical peptide (WO 98/20036). WO 97/35196 describes a method for isolating affinity ligands, in which bound ligands are selectively isolated by contacting a phage display library with a first solution that allows binding of the ligand to a target molecule and then with a second solution where affinity ligand does not bind to the target molecule. WO 97/46251 describes a method for isolating high affinity-binding phages in which a random phage display library is treated by biopanning using an affinity-purified antibody, followed by isolation of bound phages, and then by micropanning in the wells of microplates. There is also a report published on the use of Staphylococcus aureus protein A as an affinity tag (Li et al., Mol. Biotech., 9: 187 (1998)). WO 97/47314 describes the use of substrate subtraction library in identifying enzymatic specificity using a combinatorial library which may be a phage display library. WO 97/09446 describes a method for selecting enzymes that are suitable as a washing reagent to be used in phage display. Other methods for selecting proteins that bind in a specific manner are described in U.S. Pat. Nos. 5,498,538 and 5,432, 018, and WO 98/15833. Methods for constructing and screening peptide libraries are described in U.S. Pat. Nos. 5,723, 286, 5,432,018, 5,580,717, 5,427,908, 5,498,530, 5,770,434, 5,734,018, 5,698,426, 5,763,192, and 5,723,323.

Furthermore, there are known techniques for obtaining human antibodies by panning with a human antibody library. For example, using a phage display method, the variable regions of human antibodies can be expressed as single chain antibodies (scFvs) on the surface of phages to select phages that bind to an antigen. The DNA sequences encoding the variable regions of human antibodies that bind to the antigen can be determined by analyzing the genes of selected phages. When the DNA sequences of scFvs that bind to the antigen are identified, human antibodies can be prepared by constructing appropriate expression vectors carrying these sequences and expressing the antibodies in adequate hosts introduced with the expression vectors. Such methods are already known (see WO 92/01047, WO 92/20791, WO 93/06213, WO 93/11236, WO 93/19172, WO 95/01438, and WO 95/15388).

As an alternative method, the phage display technique (McCafferty et al., Nature 348: 552-553 (1990)) can be used to produce human antibodies and antibody fragments in vitro from the immunoglobulin variable (V) domain gene repertoire of a non-immunized donor. Using this technique, an antibody V domain gene is cloned in frame with a coat protein gene of filamentous bacteriophage, for example, M13 or fd, and then displayed as a functional antibody fragment on the surface of phage particles. Since filamentous particles contain a single-stranded DNA copy of the phage genome, screening based on the functional properties of antibody results in selection of genes encoding an antibody having the properties. Thus, such phages mimic some characteristics of B cells. Phage display can be carried out in various modes; see, for example, Johnson, Kevin S, and Chiswell, David J., Current Opinion in Structural Biology 3: 564-571 (1993). There are some sources of V gene segments available for phage display. Clackson et al. (Nature, 352: 624-628 (1991)) have isolated numerous various anti-oxazolone antibodies from a small random combinatorial library of V genes derived from spleens of immunized mice. The V gene repertoire of a non-immunized human donor can be constructed, and antibodies against numerous various antigens (including self antigens) can be isolated by using the technique described in either of the following documents without modification: Marks et al., J. Mol. Biol. 222: 581-597 (1991) or Griffith et al., EMBO J. 12: 725-734 (1993). See also U.S. Pat. Nos. 5,565,332 and 5,573,905.

The antibodies of the present invention also include functional antibody fragments such as Fab, Fab', F(ab')$_2$, Fv, scFv, dsFv, Diabodies, and sc(Fv)2. Multimers (for example, dimers, trimers, tetramers, and polymers) of such a functional antibody fragment are also included in the antibodies of the present invention.

Fab is a fragment with a molecular weight of about 50,000 that consists of L-chain and H-chain variable regions, and an H chain fragment containing $C_H1$ domain and a portion of hinge region. Fab is obtained by digesting IgG with papain in the presence of cysteine. In the present invention, an antibody described above can be digested with papain to prepare such Fab. Alternatively, a DNA encoding a portion of H chain and the L chain of an antibody described above is inserted into an appropriate vector. Fab can be prepared from transformants obtained by transformation using the vector.

Fab' is a fragment with a molecular weight of about 50,000 obtained by cleaving the disulfide bond between the H chains of F(ab')$_2$ described below. In the present invention, such F(ab')$_2$ can be obtained by treating an above-described antibody by pepsin digestion, followed by cleavage of disulfide bond with a reducing agent. Alternatively, like Fab, Fab' can be prepared by genetic engineering using DNA encoding Fab'.

F(ab')$_2$ is a fragment with a molecular weight of about 100,000 obtained by digesting IgG with pepsin. F(ab')$_2$ is constituted by two (Fab') fragments linked together via disulfide bond, each of which consists of L-chain and H-chain variable regions, and an H chain fragment containing $C_H1$ domain and a portion of hinge region. In the present invention, F(ab')$_2$ can be prepared by digesting an above-described antibody with pepsin. Alternatively, like Fab, F(ab')$_2$ can be prepared by genetic engineering using F(ab')$_2$-encoding DNAs.

Fv can be prepared by digesting an antibody into antibody fragments with an enzyme, for example, papain or pepsin. Alternatively, genes encoding antibody fragments are constructed and inserted into an expression vector. Fv can be expressed in appropriate host cells using the vector (see, for example, Co, M. S. et al., J. Immunol. 152, 2968-2976 (1994); Better, M. and Horwitz, A. H. Methods in Enzymology 178, 476-496 (1989); Plueckthun, A. and Skerra, A. Methods in Enzymology 178, 476-496 (1989); Lamoyi, E., Methods in Enzymology 121, 652-663 (1989); Rousseaux, J. et al., Methods in Enzymology 121, 663-669 (1989); Bird, R. E. et al., TIBTECH 9, 132-137 (1991)).

scFv is a single-chain antibody fragment in which the C terminus of one Fv chain consisting of H-chain and L-chain variable regions is linked via an appropriate peptide linker to the N terminus of the other Fv chain. Such peptide linkers include, for example, flexible $(GGGGS)_3$. For example, a DNA encoding an scFv antibody is constructed using DNAs encoding the H-chain variable region and L-chain variable region of an above-described antibody and a DNA encoding a peptide linker, and then inserted into an appropriate vector. Transformants are obtained by transformation with the resulting vector. scFv can be prepared from the transformants.

dsFv is an Fv fragment whose H-chain and L-chain variable regions are stabilized with a disulfide bond formed by introducing Cys residues at appropriate positions in the H-chain and L-chain variable regions. In each chain, the position at which Cys residue is to be introduced is determined based on the conformation predicted by molecular modeling. In the present invention, for example, the conformation is predicted from the amino acid sequences of H-chain and L-chain variable regions of an above-described antibody. DNAs are constructed to encode H-chain and L-chain variable regions that have been introduced with mutations based on the prediction, and inserted into an appropriate vector. Transformants are obtained by transformation with the resulting vector. dsFv can be prepared from the transformants.

Furthermore, multimers of antibody fragments can be prepared by linking scFv antibodies, dsFv antibodies, and the like via appropriate linkers, or fusing them to streptavidin. Fusion antibodies or labeled antibodies can be prepared from the antibodies (including antibody fragments) of the present invention by fusing or linking the antibodies with low molecular weight compounds, proteins, labeling substance, or the like. Such labeling substances include radioactive substances such as $^{125}I$.

Diabody refers to a bivalent antibody fragment constructed by gene fusion (Holliger P et al., Proc. Natl. Acad. Sci. USA, 90: 6444-6448 (1993); EP 404,097; WO 93/11161). Diabodies are dimers consisting of two polypeptide chains, where each polypeptide chain has a VL and a VH linked via a linker short enough to prevent interaction of these two domains, for example, a linker of about five residues. The VL and VH linked together in a single polypeptide chain will form a dimer because the linker between them is too short to form a single-chain variable region fragment. As a result, the polypeptide chains form a dimer, and thus the diabody has two antigen binding sites. Diabodies can be prepared by treating an antibody with an enzyme, for example, papain or pepsin, to generate antibody fragments, or by constructing DNAs encoding those antibody fragments and introducing them into expression vectors, followed by expression in an appropriate host cell (see, for example, Co, M. S. et al., J. Immunol. 152, 2968-2976 (1994); Better, M. and Horwitz, A. H., Methods Enzymol. 178, 476-496 (1989); Pluckthun, A. and Skerra, A., Methods Enzymol. 178, 497-515 (1989); Lamoyi, E., Methods Enzymol. 121, 652-663 (1986); Rousseaux, J. et al., Methods Enzymol. 121, 663-669 (1986); Bird, R. E. and Walker, B. W., Trends Biotechnol. 9, 132-137 (1991)).

sc(Fv)2 is a single-chain minibody produced by linking two VHs and two VLs using linkers and such (Hudson et al., J. Immunol. Methods 231: 177-189 (1999)). sc(Fv)$_2$ can be produced, for example, by linking scFvs via a linker.

The antibodies of the present invention also include fusion proteins in which an above-described antibody is fused with other peptides or proteins. The fusion protein can be prepared by linking a polynucleotide encoding an antibody of the present invention with a polynucleotide encoding a different peptide or polypeptide in frame, and introducing this into an expression vector and expressing it in a host. It is possible to use techniques known to those skilled in the art. Such a peptide or polypeptide to be fused with an antibody of the present invention include known peptides, for example, such as FLAG (Hopp, T. P. et al., BioTechnology 6, 1204-1210 (1988)), 6×His consisting of six His (histidine) residues, 10×His, influenza hemagglutinin (HA), human c-myc fragment, VSV-GP fragment, p18HIV fragment, T7-tag, HSV-tag, E-tag, SV40 T antigen fragment, lck tag, α-tubulin fragment, B-tag, and Protein C fragment. Furthermore, polypeptides to be fused with an antibody of the present invention include, for example, GST (glutathione-S-transferase), HA (influenza hemagglutinin), β-galactosidase, and MBP (maltose-binding protein).

The antibodies of the present invention also include antibodies linked to a labeling substance.

Such labeling substances include, but are not limited to, enzymatic luminescence (luciferase), luminescent low-molecular-weight substances, fluorescent proteins, fluorescent low-molecular-weight substances, and radionuclides. Such radionuclides include, but are not limited to, γ-ray emitting nuclides such as $^{51}Cr$, $^{59}Fe$, $^{57}Co$, $^{67}Ga$, $^{75}Se$, $^{81m}Kr$, $^{99m}Tc$, $^{111}In$, $^{125}I$, $^{131}I$, $^{133}Xe$, and $^{201}Tl$, and positron-emitting nuclides such as $^{11}C$, $^{13}N$, $^{15}O$, $^{18}F$, $^{35m}Cl$, $^{76}Br$, $^{45}Ti$, $^{48}V$, $^{60}Cu$, $^{61}Cu$, $^{62}Cu$, $^{66}Ga$, $^{89}Zr$, $^{94m}Tc$, and $^{124}I$. "m" represents nuclear isomer, which is apparent to those skilled in the art.

Fluorescent labels and luminescent labels include those using enzymatic luminescence (luciferase) and those using fluorescence (fluorescent proteins such as GFP, DsRed, and Kusabira Orange; and fluorescent low-molecular-weight substances such as FITC, Cy5.5, and Alexa Fluor 750).

When enzymatic luminescence (luciferase) is used, it is necessary to administer a substrate separately.

In particular, labels that have reduced influence from the animal's intrinsic fluorescence, and labels that emit a signal with high skin permeability are more preferred.

The present invention also provides DNAs encoding an antibody of the present invention, vectors inserted with the DNAs, and transformed cells introduced with the vectors. The vectors include, for example, M13 vectors, pUC vectors, pBR322, pBluescript, and pCR-Script. Alternatively, when the objective is to subclone and excise cDNAs, the vectors include pGEM-T, pDIRECT, and pT7, in addition to those described. DNAs encoding an antibody of the present invention, vectors inserted with the DNAs, and transformed cells introduced with the vectors are prepared by known methods.

DNAs encoding an antibody of the present invention that binds to the oxidized LDL/β$_2$GPI complex include the following DNAs:

(a) a DNA encoding a heavy chain having the nucleotide sequence of SEQ ID NO: 5;

(b) a DNA encoding a light chain having the nucleotide sequence of SEQ ID NO: 10;

(c) a DNA encoding a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4; and (d) a DNA encoding a light chain that comprises CDR1 having the amino acid sequence of SEQ ID NO: 7, CDR2 having the amino acid sequence of SEQ ID NO: 8, and CDR3 having the amino acid sequence of SEQ ID NO: 9.

When an expression vector is used for expression in *E. coli*, for example, it should have the above-described characteristics which allow its amplification in *E. coli*. Additionally, when the host is *E. coli* such as JM109, DH5α, HB101, or XL1-Blue, the vector must have a promoter that allows efficient expression in *E. coli*, for example, lacZ promoter (Ward et al. Nature 341: 544-546 (1989); FASEB J. 6: 2422-2427 (1992)), araB promoter (Better et al. Science 240:1041-1043 (1988)), or T7 promoter. The vector also includes pGEX-5X-1 (Pharmacia), "QIAexpress system" (QIAGEN), pEGFP, and pET (for this vector, BL21, a strain expressing T7 RNA polymerase, is preferably used as the host), in addition to the above-described vectors.

Furthermore, the vector may comprise a signal sequence for polypeptide secretion. When producing proteins into the periplasm of *E. coli*, the pelB signal sequence (Lei, S. P. et al. J. Bacteriol. 169: 4379 (1987)) may be used as a signal sequence for protein secretion. The vector can be introduced into host cell, for example, by the calcium chloride method or electroporation.

In addition to *E. coli* expression vectors, the vector includes, for example, expression vectors derived from mammals (for example, pcDNA3 (Invitrogen), pEGF-BOS (Nucleic Acids Res. 18(17): 5322 (1990)), pEF, and pCDM8), insect cells (for example, "Bac-to-BAC baculovirus expression system" (GIBCO-BRL), pBacPAK8), plants (for example, pMH1 and pMH2), animal viruses (for example, pHSV, pMV, and pAdexLcw), retroviruses (for example, pZIPneo), yeasts (for example, "*Pichia* Expression Kit" (Invitrogen), pNV11, and SP-Q01), and *Bacillus subtilis* (for example, pPL608 and pKTHSO).

In order to express proteins in animal cells, such as CHO, COS, and NIH3T3 cells, the vector must have a promoter necessary for expression in such cells, for example, SV40 promoter (Mulligan et al. Nature 277:108 (1979)), MMTV-LTR promoter, EF1α promoter (Mizushima et al. Nucleic Acids Res. 18: 5322 (1990)), CMV promoter, etc). It is even more preferable that the vector carries a gene for selecting transformants (for example, a drug-resistance gene that enables discrimination by a drug (such as neomycin and G418)). Vectors having such characteristics include, for example, pMAM, pDR2, pBK-RSV, pBK-CMV, pOPRSV, and pOP13.

In addition, the following method can be used for stable gene expression and gene amplification in cells: CHO cells deficient in a nucleic acid synthesis pathway are introduced with a vector (for example, pCHOI) that carries a DHFR gene which compensates for the deficiency, and the gene is amplified using methotrexate (MTX). Alternatively, the following method can be used for transient gene expression: COS cells whose chromosome contains a gene for expression of SV40 T antigen are transformed with a vector (such pcD) having an SV40 origin of replication. It is also possible to use replication origins derived from polyoma virus, adenovirus, bovine papilloma virus (BPV), or such. To increase gene copy number in host cells, the expression vectors may further contain selection markers such as aminoglycoside transferase (APH) gene, thymidine kinase (TK) gene, *E. coli* xanthine-guanine phosphoribosyltransferase (Ecogpt) gene, and dihydrofolate reductase (dhfr) gene.

Host cells to be introduced with the vectors are not particularly limited, and include, for example, *E. coli* and various types of animal cells. The host cells can be used, for example, as production systems for expressing and producing the antibodies of the present invention. The polypeptide production systems include in vitro and in vivo production systems. The in vitro production systems include production systems using eukaryotic or prokaryotic cells.

When eukaryotic cells are used, for example, animal cells, plant cells, and fungal cells can be used as the host. Such animal cells include mammalian cells (for example, CHO (J. Exp. Med. 108, 945 (1995)), COS, 3T3, myeloma, baby hamster kidney (BHK), HeLa, and Vero), amphibian cells (for example, *Xenopus* oocyte (Valle, et al., Nature 291, 338-340 (1981))), and insect cells (for example, Sf9, Sf21, and Tn5). In the present invention, CHO-DG44, CHO-DXB11, COST cells, and BHK cells are preferably used. CHO cells are particularly preferred for large-scale expression in animal cells. The vectors can be introduced into host cells, for example, by calcium phosphate methods, DEAE-dextran methods, methods using cationic liposome DOTAP (Boehringer-Mannheim), electroporation, and lipofection.

The plant cells include, for example, *Nicotiana tabacum*-derived cells, which are known as a protein production system and can be cultured as a callus. The fungal cells include yeasts, for example, the genus *Saccharomyces* such as *Saccharomyces cerevisiae* and *Saccharomyces pombe*; and filamentous bacteria, for example, the genus *Aspergillus* such as *Aspergillus niger*.

When prokaryotic cells are used, production systems using bacterial cells are available. Such bacterial cells include *E. coli*, for example, JM109, DH5a, and HB101, and *Bacillus subtilis*. The antibodies of the present invention can be prepared in vitro by culturing cells transformed with a DNA of the present invention and purifying the antibodies by conventional methods that are routinely used by those skilled in the art.

The present invention also provides host organisms that harbor a vector carrying a nucleic acid encoding an antibody of the present invention. The host organisms of the present invention are useful in producing recombinant antibodies. The host organisms of the present invention include goats. For example, transgenic goats of the present invention can be created by the method described below. Specifically, a fusion gene is constructed by inserting an antibody gene in frame within a gene encoding a protein (goat casein or such) intrinsically produced in milk. DNA fragments comprising the fusion gene which contains the inserted antibody gene are injected into goat embryos, and the resulting embryos are introduced into female goats. The antibodies of the present invention can be prepared from milk produced by transgenic animals born by the goats that received the embryos, or produced from progenies of these animals. Hormones can be given to the transgenic goats to increase the amount of milk containing the antibodies of the present invention produced by the goats (Ebert, K. M. et al., Bio/Technology 12, 699-702 (1994)).

The present invention provides imaging agents for visualizing arteriosclerotic sites, which contain an antibody that binds to the oxidized LDL/$\beta_2$GPI complex. The present invention also provides imaging methods for visualizing arteriosclerotic sites, which comprise a step of administering an antibody of the present invention that binds to the oxidized LDL/$\beta_2$GPI complex to mammals. The imaging agents of the present invention are administered to mammals to visualize arteriosclerotic sites. Such mammals include humans and nonhuman mammals (for example, mice, rats, hamsters, rabbits, pigs, and monkeys). The imaging agents of the present invention are useful in diagnosing arteriosclerosis. The imaging agents of the present invention can be used both in vivo and in vitro.

Arteriosclerotic symptoms are roughly divided into atheroma and calcified lesion. Atheroma sites in arteriosclerosis are especially stained by the imaging agents of the present invention.

Atheroma is a pathological condition of arteriosclerosis. Macrophages are known to specifically take up via receptor oxidized LDL which contains a large amount of cholesterol, and thereby become foamy. The foamy macrophages accumulate and form plaques (atheromas) on the intima of a blood vessel.

The imaging agent of the present invention is prepared by linking an imaging label or probe to an antibody that binds to the oxidized LDL/$\beta_2$GPI complex, in particular, preferably antibody 3H3. The imaging label or probe enables direct or indirect monitoring.

After in vivo administration (for example, intravenous administration) of an above-described probe, the distribution or amount accumulated can be assessed using an imagining device such as PET, SPECT, or CCD camera.

Furthermore, in recent years, computer-aided tomography (computed tomography; "CT" also refers to computed tomography) has been applied in a clinical setting such as for disease diagnosis. Computer-aided tomography is a technology for generating an image of the interior of an object by scanning the object using a source of penetrating radiation, and processing the data in a computer.

The CT technology is a technique for obtaining two-dimensional cross sectional patterns of objects (cross sections, etc.) by recording sectional images with positron emission tomography (PET), single photon emission computed tomography (SPECT), magnetic resonance imaging (MRI), or the like. These examination techniques are often used not only for obtaining sectional images, but also for presenting three dimensional graphic images by integrating the two-dimensional images using the advanced computer-assisted image processing technology. Thus, the examination techniques are powerful tools for specifying the three-dimensional location of lesions, diagnosis, decision of operative strategy, and so on.

For example, simple CT is used to obtain images by irradiating X ray or the like without using any contrast agent. Tissue edema, morphological abnormalities of bone, morphologies, and the like can be observed without using any contrast agent. Meanwhile, enhanced CT refers to CT in which images are taken after a contrast agent or the like having high X-ray absorption is injected into a blood vessel. Enhanced CT can be used to observe morphologies of blood vessels and tissues rich in blood flow. Furthermore, the so-called next-generation CT has been developed, and it can be used alone or in combination to detect the imaging agents of the present invention. Such next-generation CT is not particularly limited, and includes, for example, helical CT in which the irradiation source moves in a spiral manner, and multi-detector computed tomography (MDCT) (also referred to as multi-slice CT (MSCT)) in which detectors are arranged in multiple rows in the direction of body axis.

When the labeled imaging probe (an imaging agent of the present invention) is a radionuclide with high X-ray absorption, CT can be used alone as a detector.

Such labeling substances include, but are not limited to, enzymatic luminescence (luciferase), luminescent low-molecular-weight substances, fluorescent proteins, fluorescent low-molecular-weight substances, and radionuclides. Such radionuclides include, but are not limited to, γ-ray emitting nuclides such as $^{51}$Cr, $^{59}$Fe, $^{57}$Co, $^{67}$Ga, $^{75}$Se, $^{81m}$Kr, $^{99m}$Tc, $^{111}$In, $^{125}$I, $^{131}$I, $^{133}$Xe, and $^{201}$Tl, and positron-emitting nuclides such as $^{11}$C, $^{13}$N, $^{15}$O, $^{18}$F, $^{35m}$Cl, $^{76}$Br, $^{45}$Ti, $^{48}$V, $^{60}$Cu, $^{61}$Cu, $^{62}$Cu, $^{66}$Ga, $^{89}$Zr, $^{94m}$Tc, and $^{124}$I, "m" represents nuclear isomer, which is apparent to those skilled in the art. In particular, indium-111, technetium-99m, and iodine-131 can be particularly preferably used in two-dimensional scanning or single photon emission computed tomography (SPECT). Positron-emitting nuclide labels, for example, fluoride-19 can be particularly preferably used in positron emission tomography. Paramagnetic ions, for example, gadolinium (III) and manganese (II) can be particularly preferably used in magnetic resonance imaging (MRI).

Such labeling substances include fluorescent labels, those using enzymatic luminescence (luciferase), and those using fluorescence (fluorescent proteins such as GFP, DsRed, and Kusabira Orange; and fluorescent low-molecular-weight substances such as, FITC, Cy5.5, and Alexa Fluor 750).

When enzymatic luminescence (luciferase) is used, it is necessary to administer a substrate separately.

In particular, labels that have reduced influence from the animal's intrinsic fluorescence are preferred, and labels that emit a signal with high skin permeability are more preferred.

Magnetic resonance imaging (MRI), PET, and SPECT are used as an imaging detector. In particular, when fluorescent probes are used, CCD camera is preferably used as the monitoring device in terms of low invasiveness.

For this reason, labels that emit light at a wavelength detectable by CCD camera, for example, about 350 to 900 nm, are preferred. Furthermore, devices that can be used to determine the intensity of light source inside the body based on values obtained by monitoring the body surface of a test animal with a CCD camera are preferred. When fluorescent labels are used, the image may be a reflection fluorescence image or transmission fluorescence image; however, it is preferable to capture both images. Furthermore, the fluorescence images can be observed three-dimensionally by superimposing multi-directionally recorded fluorescence images (regardless of reflection or transmission) and integrating information of the radiation source into the superimposed images. This processing is preferred because it enables reproduction of accurate three-dimensional locations and distribution. The three-dimensional images obtained by this method can also be further superimposed with CT images.

When the labeled imaging probe is linked to a radionuclide with high X-ray absorption, CT can be used alone as the imaging detector (for example, PET or SPECT) as described above, and can also be used to determine the site, accumulated amount, and distribution of arteriosclerotic plaques.

Alternatively, following in vivo administration (for example, intravenous administration) of the-above described labeled imaging probe, the labeled probe may be observed by CT alone or in combination with CCD. When CT is used in combination with CCD, for example, a CCD image of fluorescently labeled probe is superimposed with an image of simple CT (and/or an image of enhanced CT). Specifically, CT images resulting from simple-CT image extraction of organs such as bones and lungs (and/or enhanced-CT image extraction of blood vessels and tissues) are integrated with fluorescent probe images of major arterial lesions such as in the heart. This enables more accurate understanding of the site, accumulated amount, and distribution of arteriosclerotic plaques, three-dimensional positional relationships relative to tissues and blood vessels, and accurate three-dimensional images (localization) of arteriosclerotic plaques.

The imaging agents of the present invention can be formulated, in addition to the antibodies, with pharmaceutically acceptable carriers by known methods. For example, the agents can be used parenterally, when the antibodies are formulated in a sterile solution or suspension for injection using water or any other pharmaceutically acceptable liquid. For example, the agents can be formulated by appropriately combining the antibodies of the present invention with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical practices. The content of active ingredient in such a formulation is adjusted so as to contain an appropriate dose within the specified range.

Sterile compositions for injection can be formulated using vehicles such as distilled water for injection, according to standard formulation protocols.

Aqueous solutions to be used for injection include, for example, physiological saline and isotonic solutions containing glucose or other adjuvants such as D-sorbitol, D-mannose, D-mannitol, and sodium chloride. They may be used in combination with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. They may also be formulated with buffers, for example, phosphate buffer or sodium acetate buffer; analgesics, for example, procaine hydrochloride; stabilizers, for example, benzyl alcohol or phenol; or antioxidants. The prepared injections are typically aliquoted into appropriate ampules.

The administration is preferably parenteral, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected depending on the patient's age and symptoms. The dosage of the imaging agents of the present invention can be selected, for example, from the range of 0.0001 to 1,000 mg per kg of body weight for each administration. Alternatively, the dosage may be, for example, in the range of 0.001 to 100,000 mg/person. However, the dosage is not limited to these values.

The dose and method of administration vary depending on the subject's body weight, age, symptoms, and intensity of fluorescent labeling per mg antibody/sensitivity of detection device, and can be appropriately selected by those skilled in the art.

The present invention also provides imaging kits for visualizing arteriosclerotic sites, which comprise an antibody of the present invention which binds to the oxidized LDL/$\beta_2$GPI complex. The kits of the present invention visualize arteriosclerotic sites when administered to subjects. The above-described kits contain in addition to an antibody of the present invention, for example, injectors (apparatuses for drip infusion), adjuvants for suppressing non-specific adsorption (for example, albumin), and such, without limitation thereto.

The kits may also contain items generally contained in kits, such as instruction manuals, appropriate containers, and control reagents used in imaging.

The present invention provides methods of screening for candidate compounds as therapeutic agent for treating arteriosclerosis, which comprise the steps of:

(a) administering to a nonhuman animal model of arteriosclerosis a candidate compound and an antibody of the present invention which binds to an oxidized LDL/O$_2$GPI complex, for example, administering a candidate compound to a nonhuman animal model of arteriosclerosis that has been administered with an antibody of the present invention which binds to the oxidized LDL/$\beta_2$GPI complex, (b) visualizing arteriosclerotic plaques in a nonhuman animal model of arteriosclerosis administered with the antibody and candidate compound, and in a nonhuman animal model of arteriosclerosis administered with the antibody but not with the candidate compound;

(c) comparing arteriosclerotic plaques (for example, the size or site of arteriosclerotic plaques) between a nonhuman animal model of arteriosclerosis administered with the antibody and candidate compound and a nonhuman animal model of arteriosclerosis administered with the antibody but not with the candidate compound; and (d) selecting a candidate compound that reduces or eliminates arteriosclerotic plaques in a nonhuman animal model of arteriosclerosis administered with the antibody and candidate compound as compared to a nonhuman animal model of arteriosclerosis administered with the antibody but not with the candidate compound.

Each step is performed using known techniques or techniques described above.

Candidate compounds that can be used in the screening methods of the present invention include, but are not limited to, purified proteins (including antibodies), expression products of gene libraries, synthetic peptide libraries, DNA and RNA libraries (including functional nucleic acids such as aptamers and siRNAs), cell extracts, cell culture supernatants, and synthetic low-molecular-weight compound libraries.

Nonhuman animal models of disease that can be used in the screening methods of the present invention include, but are not limited to, mice, hamsters, rats, rabbits, pigs, and monkeys.

Arteriosclerosis model mice include, for example, transgenic mice in which a gene is overexpressed, and knockout mice that are deficient in a gene as a result of gene targeting. Arteriosclerosis models include, for example, apoE-deficient (apoE$^{-/-}$) model (apoE (apolipoprotein E) is a protein that forms LDL which is known as bad cholesterol), LDL receptor-deficient (LDLR$^{-/-}$) model, model introduced with human apoB, and model introduced with dominant apoE mutation. Such model mice also include type 2 diabetes model mice (KKAy), and arteriosclerosis model mice which are produced by feeding C57BL6 mice with a high cholesterol diet or such. The C57BL6 line is known to have the greatest tendency of developing arteriosclerosis among mice, and mice of this line sometimes show arteriosclerotic plaques by simply feeding on a high cholesterol diet.

Arteriosclerotic plaques are sometimes seen in rabbits fed a high cholesterol diet for about 2.5 months. Furthermore, LDL receptor-deficient arteriosclerosis model rabbits include WHHL rabbits.

A pig arteriosclerosis model is also known, which has a tendency to develop arteriosclerosis due to abnormality in the amino acid sequence of the LDL receptor-binding domain of apoB. Those skilled in the art can prepare arteriosclerosis model animals by referring to documents such as "Kessensho/Doumyakukoka Model Doubutu Sakuseihou (Methods for producing thrombosis/arteriosclerosis model animals), Ed., Koji Suzuki (Kinpodo)". The resulting model animals can be used in the present invention.

Compounds that reduce or eliminate arteriosclerotic plaques, which are selected by the screening methods of the present invention, are candidate compounds of therapeutic agents for arteriosclerosis. Thus, the present invention provides therapeutic agents for arteriosclerosis, which comprise as an active ingredient a substance selected by the screening methods of the present invention. The present invention also relates to the use of compounds selected by the screening methods of the present invention in manufacturing therapeutic agents for arteriosclerosis. When substances isolated by the screening methods of the present invention are used as a therapeutic agent, they can be used after they are formulated using known pharmaceutical production methods. For example, such substances are administered to patients in combination with pharmaceutically acceptable carriers or media (physiological saline, vegetable oils, emulsifiers, detergents, stabilizers, etc.). The substance is administered transdermally, nasally, transbronchially, intramuscularly, intravenously, or orally according to its properties. The dosage depends on the patient's age, weight, and symptoms, and the method of administration. However, those skilled in the art can select an appropriate dose.

The nucleotide and amino acid sequences of the antibodies described herein are shown in the Sequence Listing according to the SEQ IDs shown below.

<Antibody 3H3>
SEQ ID NO: 1, the amino acid sequence of heavy-chain variable region
SEQ ID NO: 2, the amino acid sequence of heavy chain CDR1
SEQ ID NO: 3, the amino acid sequence of heavy chain CDR2
SEQ ID NO: 4, the amino acid sequence of heavy chain CDR3
SEQ ID NO: 5, the nucleotide sequence of heavy-chain variable region
SEQ ID NO: 6, the amino acid sequence of light-chain variable region
SEQ ID NO: 7, the amino acid sequence of light chain CDR1
SEQ ID NO: 8, the amino acid sequence of light chain CDR2
SEQ ID NO: 9, the amino acid sequence of light chain CDR3
SEQ ID NO: 10, the nucleotide sequence of light-chain variable region All prior art documents cited in the specification are incorporated herein by reference.

EXAMPLES

Hereinbelow, the present invention will be specifically described with reference to the Examples, but is not to be construed as being limited to the illustrative embodiments described in the Examples.

Example 1

Preparation of Oxidized LDL/$\beta_2$GPI Complex

600 μg of human LDL (Organon Teknika Corp., Durham, N.C.) was oxidized in 2 ml of PBS containing 5 μM $CuSO_4$ at 37° C. for 12 hours. The oxidization was terminated by adding 1 mM EDTA.

0.2 mg/ml oxidized LDL described above was incubated at a final concentration of 0.2 mg/ml with human $\beta_2$GPI (purchased from Affinity Biologicals) at 37° C. for 16 hours to form the oxidized LDL/$\beta_2$GPI complex.

Example 2

Immunization with Antigen

Purified protein of human oxidized LDL/$\beta_2$GPI complex was mixed with the same amount of complete adjuvant (SIGMA; F5881). BALB/c mice (female) were immunized through footpads with the resulting emulsion at 5 to 50 μg/head every three to seven days several times. Three to five days after the final immunization, inguinal lymph nodes were excised from the mice, and fused with cells of mouse myeloma P3U1 (P3-X63Ag8U1).

Example 3

Cell Fusion, and Selection and Isolation of Monoclonal Antibody-Producing Cells

Cell fusion was carried out based on the conventional method described below. For every medium, fetal bovine serum (FBS) was used after inactivation by incubation at 56° C. for 30 minutes. P3U1 was prepared by culturing in RPMI1640-10% FBS (containing penicillin and streptomycin).

Cells from excised mouse inguinal lymph nodes were combined with P3U1 at a ratio of 10:1 to 2:1. The mixed cells were centrifuged. As a fusion enhancing agent, 50% polyethylene glycol 4000 (Merck; gas chromatography grade PEG4000, Catalog No. 9727) was added little by little to the precipitated cells while gently mixing to achieve cell fusion. Then, RPMI1640 was added little by little to the mixture with gentle mixing. The resulting mixture was centrifuged. The precipitated fused cells were appropriately diluted with HAT medium containing 15% FCS(RPMI1640, HAT-supplement (Invitrogen; 11067-030), penicillin, and streptomycin), and plated at 200 μl/well in 96-well microplates.

The fused cells were cultured in a $CO_2$ incubator (5% $CO_2$, 37° C.). When the cells were sufficiently grown as colonies, screening was carried out by sampling the culture supernatants.

In the screening, positive clones were selected by ELISA (described in Example 4) using 96-well plates coated with the human oxidized LDL/$\beta_2$GPI complex, which was the same as that used as the immunizing antigen. The clones were expanded using HT medium (RPMI1640, HT-supplement (Invitrogen; 21060-017), penicillin, and streptomycin) containing 15% FCS, and then cloned into single clones by the limiting dilution method. This screening which used the anti-human oxidized LDL/$\beta_2$GPI complex antibody as an immunogen yielded seven types of hybridoma clones including clone 3H3.

Example 4

Reactivity to Human Oxidized LDL/$\beta_2$GPI Complex and $\beta_2$GPI (ELISA)

The ELISA for detecting an anti-human oxidized LDL/$\beta_2$GPI complex antibody was carried out by the method described below. Specifically, 50 μl of 1 μg/ml oxidized LDL/$\beta_2$GPI was added to each well of microplates (Nunc; Maxisorp). The plates were incubated at 4° C. overnight to adsorb the complex, and then blocked with 1% BSA. Antibody samples were diluted using an assay buffer (1% BSA, 0.15 M NaCl/20 mM HEPES (pH 7.4)) to the antibody concentrations indicated on the horizontal axis. 50 μl of each sample was added to the wells, and the wells were incubated for 30 minutes. The solutions were discarded, and the wells were washed with 0.1% Tween 20/PBS. Then, 50 μl of 2,000-times diluted HRP-labeled anti-mouse IgG (MBL code 330) was added to each well of the plates, and incubated for 30 minutes. The solutions were discarded, and the wells were washed with 0.1% Tween 20/PBS. Then, 50 μl of substrate TMB (MOSS; TMBZ) was added, and the plates were incubated at room temperature for three minutes. After the reaction was terminated by adding 50 µl of 0.18 M sulfuric acid, detection was carried out using absorbance at 450 nm (FIG. 1A).

To detect the reactivity to $\beta_2$GPI, ELISA was carried out by the method described below. Specifically, 50 µl of 1 µg/ml $\beta_2$GPI was added to each well of microplates (Nunc; Maxisorp). The plates were incubated at 4° C. overnight to adsorb $\beta_2$GPI, and then blocked with 1% BSA. Antibody samples were diluted using the assay buffer (1% BSA, 0.15 M NaCl/20 mM HEPES (pH 7.4)) to the antibody concentrations indicated on the horizontal axis. 50 µl of each sample was added to the wells, and incubated for 30 minutes. The solutions were discarded, and the wells were washed with 0.1% Tween 20/PBS. Then, 50 µl of 2,000-times diluted HRP-labeled anti-mouse IgG (MBL code 330) was added to each well of the plates, and incubated for 30 minutes. The solutions were discarded, and the wells were washed with 0.1% Tween 20/PBS. Then, 50 µl of substrate TMB (MOSS; TMBZ) was added, and the plates were incubated at room temperature for three minutes. After the reaction was terminated by adding 50 µl of 0.18 M sulfuric acid, detection was carried out using absorbance at 450 nm (FIG. 1B).

Furthermore, various concentrations of $\beta_2$GPI (up to 50 µg/ml) were prepared and added at 50 µl/well to microplates (Nunc; Maxisorp). The plates were incubated at 4° C. overnight to adsorb $\beta_2$GPI. Then, the antibody reactivity was tested in the same manner (data not shown).

The result showed that the reactivity towards the immobilized oxidized LDL/$\beta_2$GPI complex was: 2H6>3H3, 2A12, 3D4>4C12, 1H4. Alternatively, the reactivity towards the immobilized $\beta_2$GPI was: 2H6, 3D4>2A12, 4F10. 3H3 and 4C12 were not reactive to the immobilized $\beta_2$GPI (FIGS. 1A and B).

However, when the coating concentration in microtiter plates was increased, 3H3 also exhibited reactivity (data not shown).

Next, as a method for assessing antibody reactivity, inhibition test using a free antigen was carried out to evaluate the specificity of each antibody.

Example 5

Competitive Reactivity to Free $\beta_2$GPI or Oxidized LDL/$\beta_2$GPI Complex in Solution (ELISA)

Figure 2:
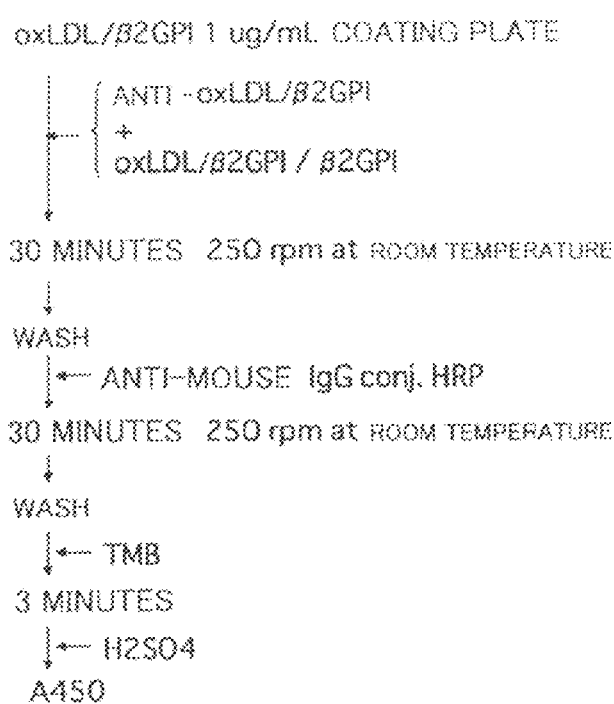
FIG. 2 is a diagram for assaying competitive nature of antigen in solution (competitive inhibition assay).
Figure 2:
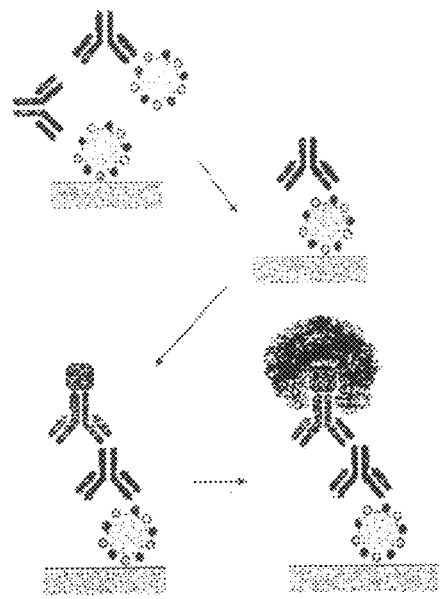

In the reactivity assay (ELISA) for immobilized human oxidized LDL/$\beta_2$GPI complex and $\beta_2$GPI, an inhibitory reaction to immobilized antigen was carried out by having oxidized LDL/$\beta_2$GPI complex or $\beta_2$GPI together when the antibodies were added in the reaction (Schematic diagram of assay system is shown in FIG. 2).

Specifically, 50 µl of 1 µg/ml $\beta_2$GPI was added to each well of microplates (Nunc; Maxisorp). The plates were incubated at 4° C. overnight to adsorb $\beta_2$GPI, and then blocked with 1% BSA. Antibody samples were diluted to appropriate concentrations using the assay buffer (1% BSA, 0.15 M NaCl/20 mM HEPES (pH 7.4)), and samples of oxidized LDL/$\beta_2$GPI complex or $\beta_2$GPI, which serves as a competitive antigen, were diluted to the antigen concentrations indicated on the horizontal axis. 25 µl each of the diluted antibody sample and antigen sample were added to the wells, and the wells were incubated for 30 minutes. The solutions were discarded, and the wells were washed with 0.1% Tween 20/PBS. Then, 50 µl of 2,000-times diluted HRP-labeled anti-mouse IgG (MBL code 330) was added to each well of the plates, and the plates were incubated for 30 minutes. The solutions were discarded, and the wells were washed with 0.1% Tween 20/PBS. Then, 50 µl of substrate TMB (MOSS; TMBZ) was added, and the plates were incubated at room temperature for three minutes. After the reaction was terminated by adding 50 µl of 0.18 M sulfuric acid, detection was carried out using absorbance at 450 nm.

Figure 3:
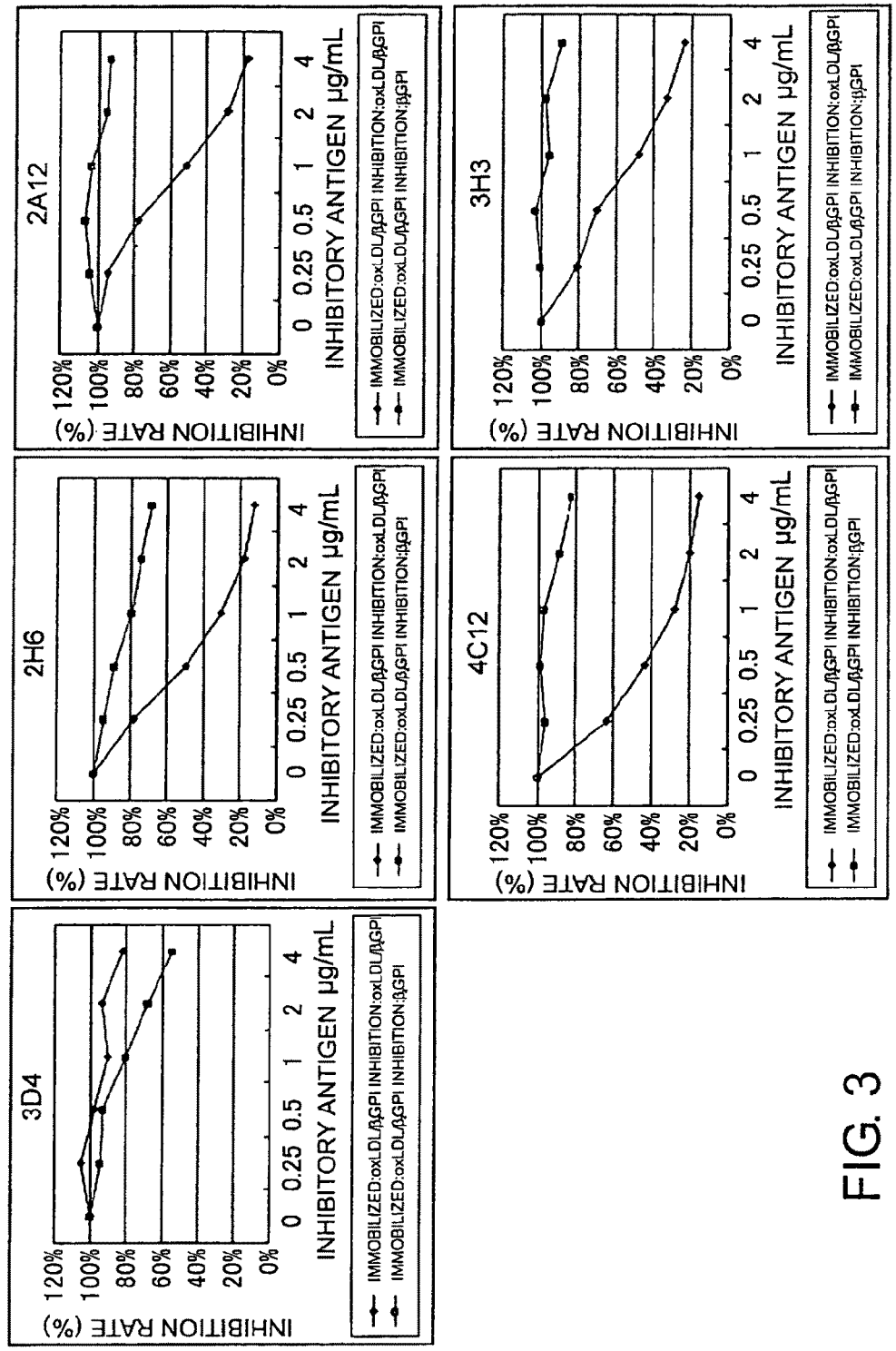
FIG. 3 is graphs showing a test of competitive inhibition by antigen. The horizontal axis indicates antigen concentration in a liquid, and the vertical axis indicates the percent inhibition (%) determined when taking the absorbance in the absence of inhibitory antigen as 100%. 3H3 and 4C12 are antibodies that recognize $\beta_2$GPI bound to oxidized LDL. These antibodies do not recognize free $\beta_2$GPI. 2H6, 3D4, and 2A12 are antibodies reactive to free $\beta_2$GPI.

The result showed that when the coexisting oxidized LDL/$\beta_2$GPI complex was the free antigen in ELISA, the binding of 3H3, 4C12, and 2A12 to immobilized oxidized LDL/$\beta_2$GPI was markedly inhibited, while $\beta_2$GPI did not inhibit the binding. On the other hand, the binding of 2H6 was inhibited when the free antigen was the oxidized LDL/$\beta_2$GPI complex, and the mixing with $\beta_2$GPI also inhibited the binding to some extent. As for 3D4, stronger inhibition was observed with $\beta_2$GPI than with oxidized LDL/$\beta_2$GPI complex as free antigen (FIG. 3).

From the results above, reactivity of antibodies can be summarized as shown in Table 1 (Table 1 is shown in Example 7). 3H3 showed similar reactivity to 4C12, but was not the same reactivity, and had different specificity.

Example 6

Immunohistochemical Staining of Arteriosclerotic Plaques with Antibodies

ApoE$^{-/-}$ mice and LDLR$^{-/-}$ mice (obtained from Jackson Lab, and maintained in the animal experiment facility at Okayama University) were fed a common diet (Oriental Yeast NMF) up to eight weeks old, and then fed a high fat diet (common diet additionally containing 1% cholesterol, 1% cholic acid, and 15% salt-free butter) for four to six months. As a result, arteriosclerotic plaques developed, and thus thickening and atheroma were observed in the thoracic or abdominal aorta. Then, these eight-month-old mice were sacrificed. Cryosections of the thoracic aorta, and aortic root and valves were prepared from the mice, and observed as samples.

The prepared cryosections were fixed with paraformaldehyde and then used in the experiment of fluorescent antibody immunostaining.

Labeling of Monoclonal Antibody with Cy5.5

Various monoclonal antibodies (1 mg/ml) were dialyzed against 0.1 M carbonate buffer (pH 9.3) at 4° C. overnight, and each was transferred into Fluorolink Cy5.5 monofunctional dye (1 tube). After 30 minutes of incubation at room temperature, the antibodies were treated with a SephadexG-25 column to yield Cy5.5-labeled antibody.

Fluorescent Immunostaining of Cryosections

Sections were fixed with 1% paraformaldehyde for five minutes, and then incubated with various monoclonal antibodies at 4° C. overnight. After washing, the sections were incubated with an FITC-labeled anti-mouse IgG or IgM antibody (secondary antibody) at room temperature for one hour. Staining with DAPI and Rhodamine Phalloidin was carried out by addition with the secondary antibody at the time of incubation. Then, the sections were observed and photographed under a fluorescent microscope.

Immunohistochemical Staining

Figure 4:
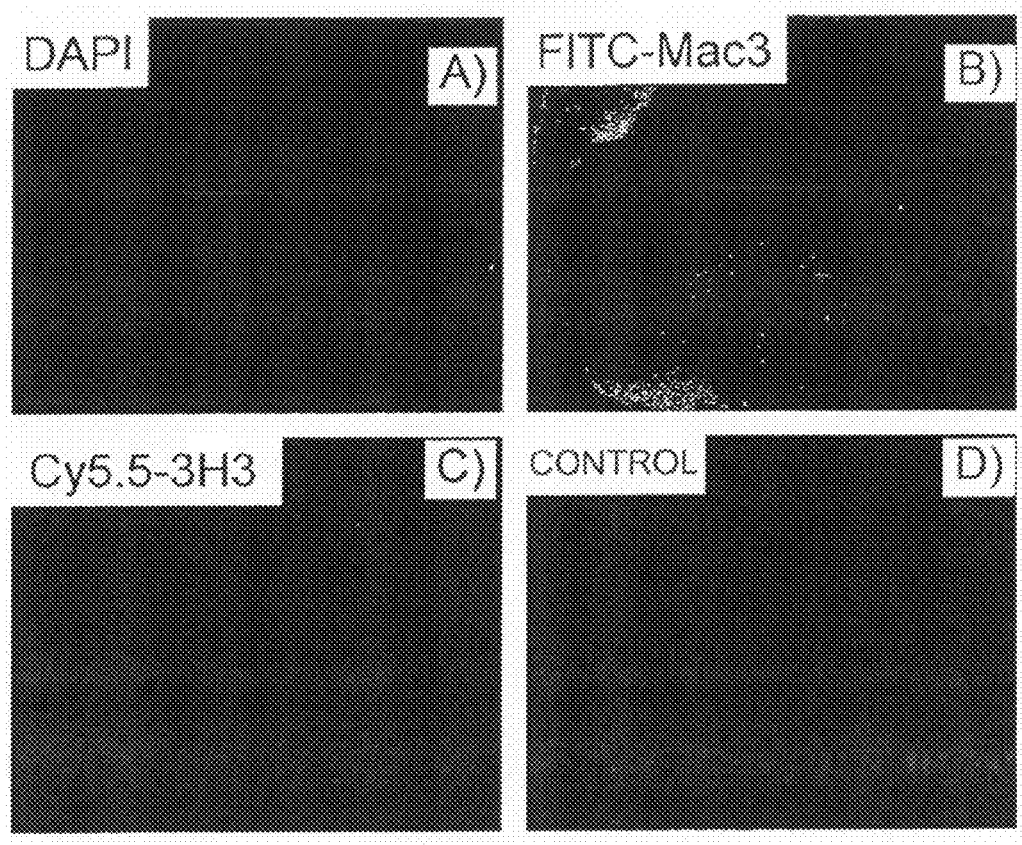
FIG. 4 is photographs showing fluorescent immunostaining of the aortic valve in arteriosclerosis-prone model mice (apoE$^{-/-}$ fed a high fat diet). (A) DAPI, nuclear stain; (B) Mac3, macrophage-specific antibody; (C), antibody 3H3; (D), control. When used in fluorescent immunostaining of C57BL6 mice fed a normal diet, Mac3 stained atheroma formed via accumulation of foamy macrophages. 3H3 stained the same areas.

The result showed that when used in fluorescent immunostaining of C57BL6 mice fed a normal diet, both antibodies 3H3 and Mac3 stained atheroma resulting from accumulation of foamy macrophages. 3H3 stained the same areas (FIG. 4).

Figure 5:
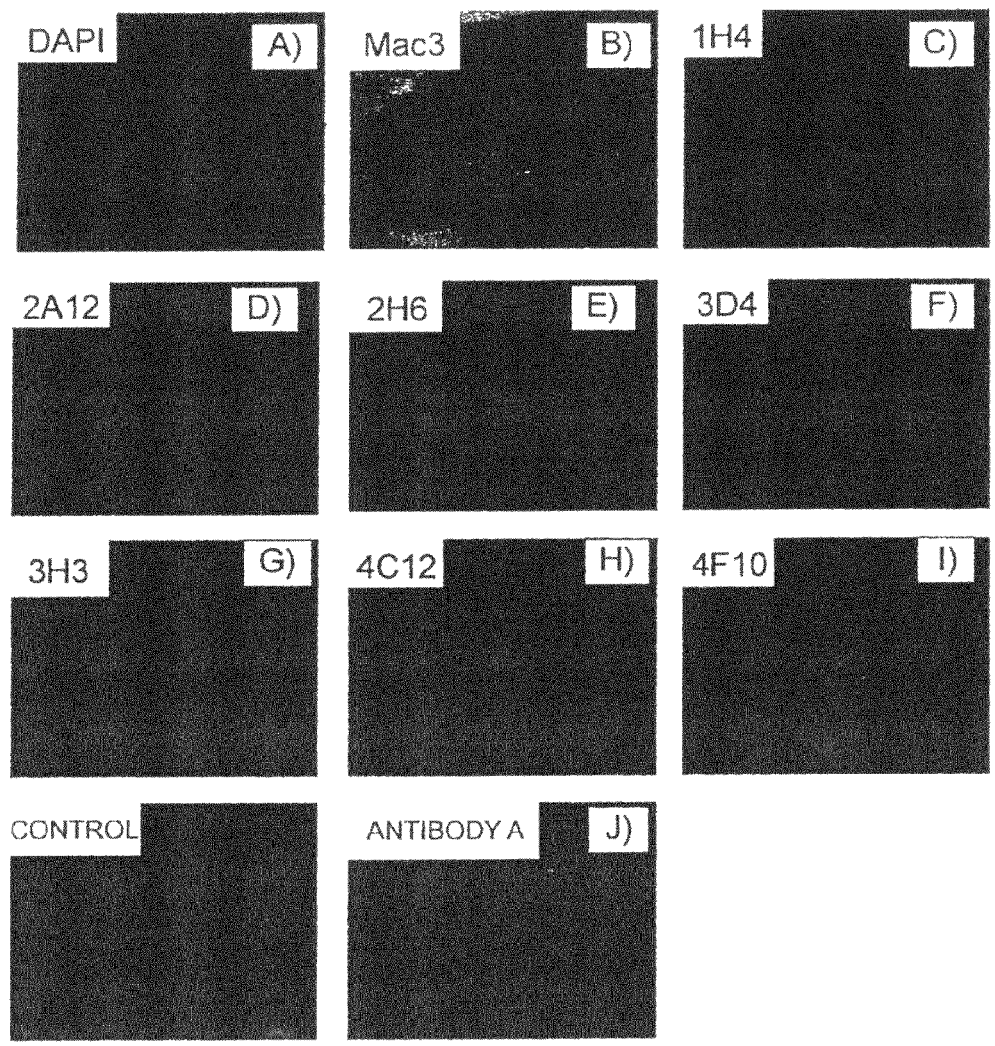
FIGS. 5A-J and Control are photographs showing fluorescent immunostaining of the aortic valve in arteriosclerosis-prone model mice (apoE$^{-/-}$ fed a high fat diet). The photographs show results of fluorescent immunostaining using other antibodies against the oxidized LDL/$\beta_2$GPI complex. Antibodies positive for atheroma in the staining were only antibodies 3H3 and A.
Figure 6:
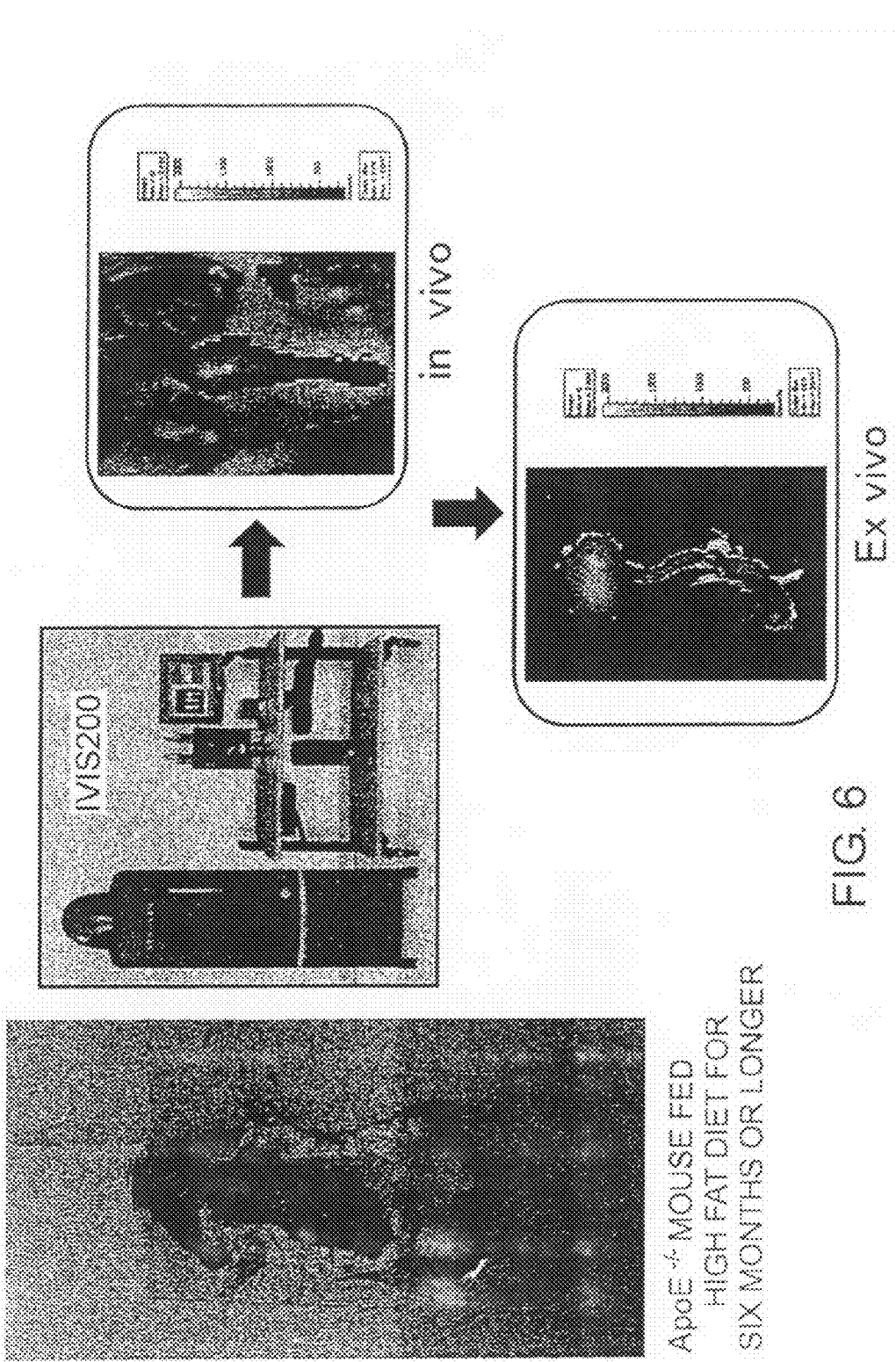
FIG. 6 is photographs showing IVIS 200 fluorescence imaging using specific antibody (reflection fluorescence microscopy). In vivo: ApoE$^{-/-}$ mice were fed a high fat diet for six months or more. Imaging agents were administered to the mice at the caudal vein. After two to 24 hours, in vivo fluorescence was observed and photographed under inhalation anesthesia using IVIS 200. The ApoE$^{-/-}$ mice were observed after shaving, because their black hair absorbs fluorescence. Ex vivo: Mice euthanized were thoracotomized. The heart and aorta were exposed, and a small incision was made in the right auricular appendage. Then, a needle was inserted into the left ventricle and the heart was perfused with 10 ml of cold PBS. The heart and aorta were excised and their reflection fluorescence microscopic images were recorded using IVIS 200.

Fluorescent immunostaining of the aortic valve in arteriosclerosis-prone model mice (apoE$^{-/-}$ fed a high fat diet) was compared to the result obtained using different antibodies that recognize the oxidized LDL/$β_2$GPI complex. Antibodies positive for atheroma in the staining were only antibodies 3H3 and A (FIG. 5).

Thus, the present invention enables arteriosclerotic plaque-specific immunostaining using various atheroma-specific monoclonal antibodies labeled with Cy5.5, Alexa, or the like.

Example 7

Imaging

In Vivo Imaging:

Imaging was performed using IVIS™ Imaging System, IVIS 200, from Xenogen (excitation, 640 nm; emission, 720 nm).

Figure 7:
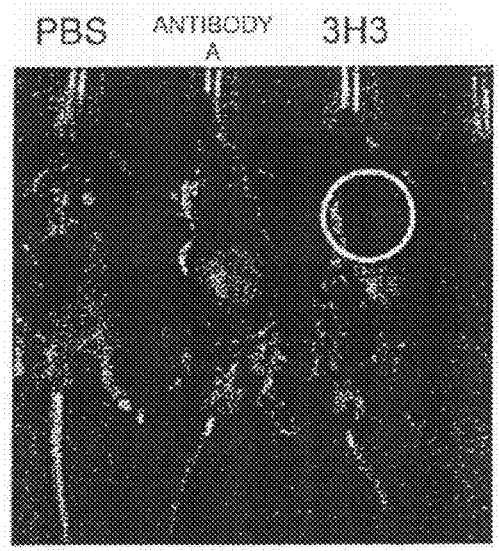
FIG. 7 is photographs showing IVIS 200 fluorescence imaging (excitation, 640 nm; emission, 720 nm). Experiment 1: physiological saline (PBS; control), Cy5.5-labeled antibody A, or Cy5.5-labeled antibody 3H3 was administered at the caudal vein to apoE$^{-/-}$ mice fed a high fat diet. Twenty four hours after administration, the mice were photographed alive for the full-body image after removing their thoracic skin. Then, the heart intact with thoracic aorta was excised and photographed. Experiment 2: Hearts and aortae excised from mice administered with PBS, Cy5.5-labeled antibody 2A12, or y5.5-labeled antibody 3H3. Administered 3H3 intensely stained the aortic root. Antibody A also stained to some extent; however, the fluorescence intensity is weaker as compared to 3H3. There was no stain in the case of 2A12.
Figure 7:
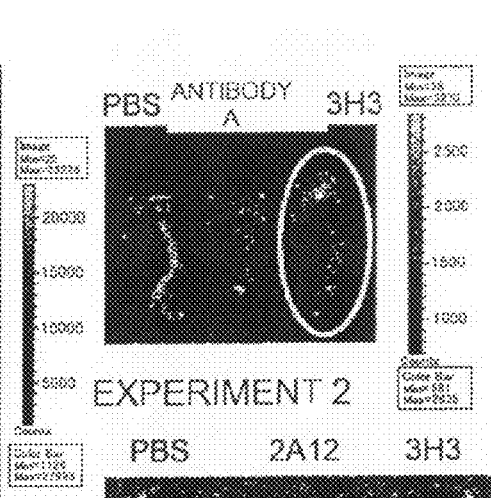
Figure 7:

Experiment 1: Cy5.5-labeled monoclonal antibody (0.25 mg/ml) was administered at 0.15 ml/head via the caudal vein to apoE$^{-/-}$ mice fed a high fat diet, which were prepared by the same method as described in Example 6. The following three were administered: physiological saline (PBS; control), Cy5.5-labeled antibody A, and Cy5.5-labeled antibody 3113. Twenty four hours after administration, the mice were photographed alive for the full-body image after removing their thoracic skin (FIG. 7).

Experiment 2: Then, the heart intact with thoracic aorta was excised and photographed (FIG. 7). The aortic root was intensely stained by 3113 administration. Antibody A also stained to some extent; however, the fluorescence intensity was weaker as compared to 3H3. There was no stain with 2A12.

Figure 10:
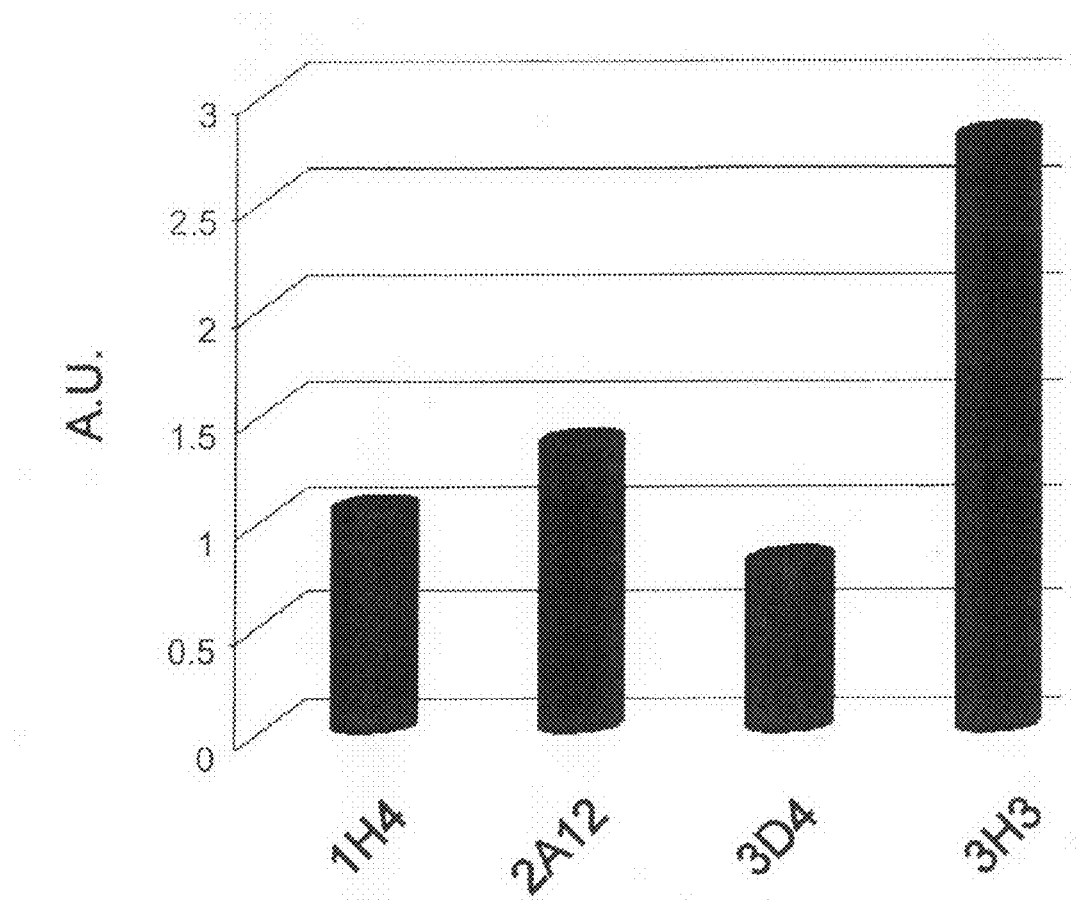
FIG. 10 is a diagram showing fluorescence intensity of Cy5.5 around the aortic root observed using IVIS 200. The fluorescence intensity was determined per unit area of the aortic root. The fluorescence of PBS-administered control mouse was taken as 1.0. When 3H3 was administered, fluorescence was three times stronger than the control. When other antibodies were administered, there was no significant change in the fluorescence intensity.

The fluorescence intensity was determined per unit area of the aortic root. The fluorescence of PBS-administered control mouse was taken as 1.0. When 3H3 was administered, fluorescence was three times stronger than the control. There was no significant change in the fluorescence intensity when other antibodies were administered (FIG. 10).

The specificity assessment of the antibodies described above is summarized in Table 1.

TABLE 1

ANTIBODIES SPECIFIC TO OXDIZED LDL/β2GPI COMPLEX

| | BINDING TO IMMOBILIZED ANTIGEN | | COMPETITIVE INHIBITION (IMMOBILIZED OXIDIZED LDL/β2GPI) | | |
|---|---|---|---|---|---|
| | β2GPI | OXIDIZED LDL/β2GPI | OXIDIZED β2GPI | OXIDIZED LDL/β2GPI | IMMUNO-STAINING |
| 1H4 | − | + | ND | ND | − |
| 2A12 | + | ++ | − | ++ | − |
| 2H6 | ++ | +++ | ++ | ++ | − |
| 3D4 | ++ | ++ | ++ | − | − |
| 3H3 | − | ++ | − | ++ | +++ |
| 4C12 | − | + | − | ++ | − |
| 4F10 | + | − | ND | ND | − |

$β_2$GPI was added as an inhibitory, competitive antigen to the immobilized oxidized LDL/$β_2$GPI complex or immobilized $β_2$GPI, and the resulting inhibition was assessed by ELISA. The result is as follows: in the case of immobilized oxidized LDL/$β_2$GPI complex, 3D4>2H6>4C12>3H3; and in the case of immobilized $β_2$GPI, 2H6>3D4 (4C12 and 3H3 bound only weakly to immobilized $β_2$GPI). 3H3 was highly specific to the free (non-denatured) form of oxidized LDL/$β_2$GPI complex in a solution.

Example 8

Analysis of Variable Region Gene of Mouse Monoclonal Antibodies that Recognize Oxidized LDL/$β_2$GPI Complex Four monoclonal antibody clones analyzed were: 3H3, 4C12, 2H6, and 3D4.

The antibody subclasses of the four clones are as follows: 3H3 and 4C12 are IgG2b; and 2H6 and 3D4 are IgG1.

Analysis of L-Chain Variable Region Gene

Hybridomas which produce four types of monoclonal antibodies (3H3, 4C12, 2H6, and 3D4) were each cultured in RPMI1640 supplemented with 10% FCS. mRNAs were obtained from the hybridomas using the QuickPrep micro mRNA purification kit (Amersham Biosciences; code 27-9255-01). The mRNAs were converted into cDNAs using the First-Strand cDNA Synthesis kit (Amersham Biosciences; code 27-9261-01). Gene amplification was achieved by PCR using the cDNAs as a template. PCR was carried out using the 11 types of primer combinations listed below. The sequences of primers MKV1 to MKV11 were designed by analyzing the signal sequences of numerous various monoclonal antibodies. Thus, the 11 types of primer sequences can cover the L chain signal of almost every monoclonal antibody. An L-chain variable region of interest is amplified by using at least a single PCR pattern selected from 11 PCR patterns using combinations of the 11 types of MKV primers with primer MKC which corresponds to the sequence of a mouse L-chain constant region.

The PCR conditions are shown below.

| | |
|---|---|
| cDNA derived from mouse hybridoma | 4 μl |
| 2.5 mM dNTPs | 4 μl |
| one of the 11 types of primers MKV1 to MKV11 (20 μM) | 2.5 μl |
| MKC primer (20 μM) | 2.5 μl |
| DMSO | 2.5 μl |
| ×10 pfu polymerase buffer | 5 μl |
| pfu polymerase | 1 μl |
| sterile water | 28.5 μl |
| Total | 50 μl |

94° C. for 2 min
94° C. for 1 min, 55° C. for 2 min, 72° C. for 2 min (30 cycles)
72° C. for 4 min
4° C., no time restriction The DNA sequences of primers are shown below.

```
                                     (SEQ ID NO: 11)
MKV1 primer:    ATGAAGTTGCCTGTTAGGCTGTTGGTGCTG (SEQ ID NO: 12)
MKV2 primer:    ATGGAGWCAGACACACTCCTGYTATGGGTG (SEQ ID NO: 13)
MKV3 primer:    ATGAGTGTGCTCACTCAGGTCCTGGSGTTG (SEQ ID NO: 14)
MKV4 primer:    ATGAGGRCCCCTGCTCAGWTTYTTGGMWTCTTG (SEQ ID NO: 15)
MKV5 primer:    ATGGATTTWCAGGTGCAGATTWTCAGCTTC
```

```
                                              (SEQ ID NO: 16)
MKV6 primer:      ATGAGGTKCYYTGYTSAGYTYCTGRGG (SEQ ID NO: 17)
MKV7 primer:      ATGGGCWTCAAGATGGAGTCACAKWYYCWGG (SEQ ID NO: 18)
MKV8 primer:      ATGTGGGGAYCTKTTTYCMMTTTTTCAATTG (SEQ ID NO: 19)
MKV9 primer:      ATGGTRTCCWCASCTCAGTTCCTTG (SEQ ID NO: 20)
MKV10 primer:     ATGTATATATGTTTGTTGTCTATTTCT (SEQ ID NO: 21)
MKV11 primer:     ATGGAAGCCCCAGCTCAGCTTCTCTTCC (SEQ ID NO: 22)
MKC primer:       ACTGGATGGTGGGAAGATGG
(M = A or C; R = A or G; W = A or T; S = C
or G; Y = C or T; K = G or T)
```

Combinations of PCR primers responsible for the amplification of each L-chain variable region by PCR are as follows:

3H3: MKV7-MKC

4C12: MKV7-MKC

2H6: MKV5-MKC

3D4: MKV4-MKC

The L-chain variable region genes amplified by PCR were inserted into pCR2.1 vector (Invitrogen).

The DNA nucleotide sequence of PCR2.1 vector inserted with an L-chain variable region gene was determined using a DNA sequencer (Applied Biosystems; 3130 Genetic Analyzer).

Analysis of H-Chain Variable Region Gene

Hybridomas which produce four types of monoclonal antibodies (3H3, 4C12, 2H6, and 3D4) were each cultured in RPMI1640 supplemented with 10% FCS. mRNAs were obtained from the hybridomas using the QuickPrep micro mRNA purification kit (Amersham Biosciences; code 27-9255-01). The mRNAs were converted into cDNAs using the First-Strand cDNA Synthesis kit (Amersham Biosciences; code 27-9261-01). Amplification of H chain variable region genes was achieved by PCR using the cDNAs as a template. PCR was carried out using the 12 types of primer combination listed below. The sequences of primers MHV1 to MHV12 were designed by analyzing the signal sequences of numerous various monoclonal antibodies. Thus, the 12 types of primer sequences can cover the H chain signal of almost every monoclonal antibody. An H-chain variable region of interest is amplified by using at least a single PCR pattern selected from 12 PCR patterns using combinations of the 12 types of MHV primers with primer MHCG2b or MHCG1 which corresponds to the sequence of a mouse H-chain constant region. Primer MHCG2b corresponds to the sequence of an H-chain constant region of mouse IgG2b, while primer MHCG1 corresponds to the sequence of an H-chain constant region of mouse IgG1. Thus, primer MHCG2b was used in the PCR amplification of clones 3H3 and 4C12, which are of the IgG2b subclass. Primer MHCG1 was used in the PCR amplification of clones 2H6 and 3D4, which are of the IgG1 subclass.

The PCR conditions are shown below.

| | |
|---|---|
| cDNA derived from mouse hybridoma | 4 µl |
| 2.5 mM dNTPs | 4 µl |
| one of the 12 types of primers MHV1 to MHV12 (20 µM) | 2.5 µl |
| MHCG2b or MHCG1 primer (20 µM) | 2.5 µl |
| DMSO | 2.5 µl |
| ×10 pfu polymerase buffer | 5 µl |
| pfu polymerase | 1 µl |
| sterile water | 28.5 µl |
| Total | 50 µl |

94° C. for 2 min

94° C. for 1 min, 55° C. for 2 min, and 72° C. for 2 min (30 cycles)

72° C. for 4 min

4° C., no time restriction

The DNA sequences of primers are shown below.

```
                                              (SEQ ID NO: 23)
MHV1 primer:      ATGAAATGCAGCTGGGGCATSTTCTTC (SEQ ID NO: 24)
MHV2 primer:      ATGGGATGGAGCTRTATCATSYTCTT (SEQ ID NO: 25)
MHV3 primer:      ATGAAGWTGTGGTTAAACTGGGTTTTT (SEQ ID NO: 26)
MHV4 primer:      ATGRACTTTGGGYTCAGCTTGRTTT (SEQ ID NO: 27)
MHV5 primer:      ATGGACTCCAGGCTCAATTTAGTTTTCCTT (SEQ ID NO: 28)
MHV6 primer:      ATGGCTGTCYTRGSGCTRCTCTTCTGC (SEQ ID NO: 29)
MHV7 primer:      ATGGRATGGAGCKGGRTCTTTMTCTT (SEQ ID NO: 30)
MHV8 primer:      ATGAGAGTGCTGATTCTTTTGTG (SEQ ID NO: 31)
MHV9 primer:      ATGGMTTGGGTGTGGAMCTTGCTATTCCTG (SEQ ID NO: 32)
MHV10 primer:     ATGGGCAGACTTACATTCTCATTCCTG (SEQ ID NO: 33)
MHV11 primer:     ATGGATTTTGGGCTGATTTTTTTTATTG (SEQ ID NO: 34)
MHV12 primer:     ATGATGGTGTTAAGTCTTCTGTACCTG (SEQ ID NO: 35)
MHCG2b primer:    CAGTGGATAGACTGATGGGGG (SEQ ID NO: 36)
MHCG1 primer:     CAGTGGATAGACAGATGGGGG
(M = A or C; R = A or G; W = A or T; S = C
or G; Y = C or T; K = G or T)
```

Combinations of PCR Primers Responsible for the Amplification of Each H-Chain variable region by PCR are as follows:

3H3: MHV4-MHCG2b

4C12: MKV4-MHCG2b

2H6: MHV4-MHCG1

3D4: MHV1-MHCG1

The H-chain variable region genes amplified by PCR were inserted into the pCR2.1 vector (Invitrogen).

The DNA nucleotide sequence of the PCR2.1 vector inserted with an H-chain variable region gene was determined using a DNA sequencer (Applied Biosystems; 3130 Genetic Analyzer).

Thus, the amino acid sequence of 3H3 and its CDRs were revealed, and can be used in the present invention (FIG. 11).

The amino acid and nucleotide sequences of the antibodies of the present invention are shown in the Sequence Listing according to the following SEQ IDs shown below.

<Antibody 3H3>

SEQ ID NO: 1, the amino acid sequence of heavy-chain variable region

SEQ ID NO: 2, the amino acid sequence of heavy chain CDR1

SEQ ID NO: 3, the amino acid sequence of heavy chain CDR2

SEQ ID NO: 4, the amino acid sequence of heavy chain CDR3

SEQ ID NO: 5, the nucleotide sequence of heavy-chain variable region

SEQ ID NO: 6, the amino acid sequence of light-chain variable region

SEQ ID NO: 7, the amino acid sequence of light chain CDR1

SEQ ID NO: 8, the amino acid sequence of light chain CDR2

SEQ ID NO: 9, the amino acid sequence of light chain CDR3

SEQ ID NO: 10, the nucleotide sequence of light-chain variable region

Example 9

Assessment of Image Analysis Using IVIS 200 and Three-Dimensional CT

Experiments were carried out to generate three-dimensional (localization) images of arteriosclerotic plaques by integrating computed tomography (CT) images.

Figure 9:
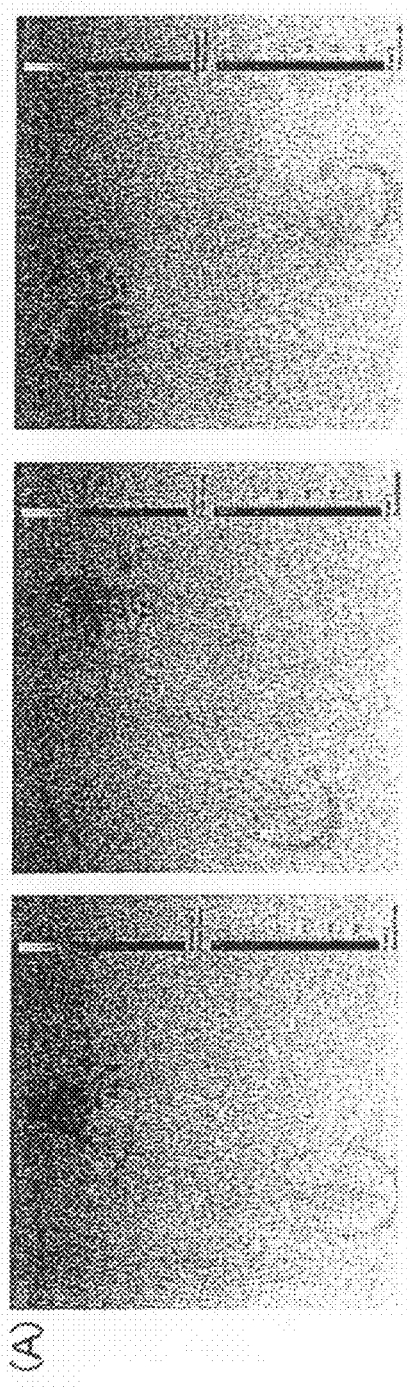
FIG. 9 is photographs showing IVIS 200 fluorescence three-dimensional images before superimposing (upper panels, A) and superimposed images generated from IVIS 200 fluorescence signal and 3D CT (bottom panels, B).
Figure 9:
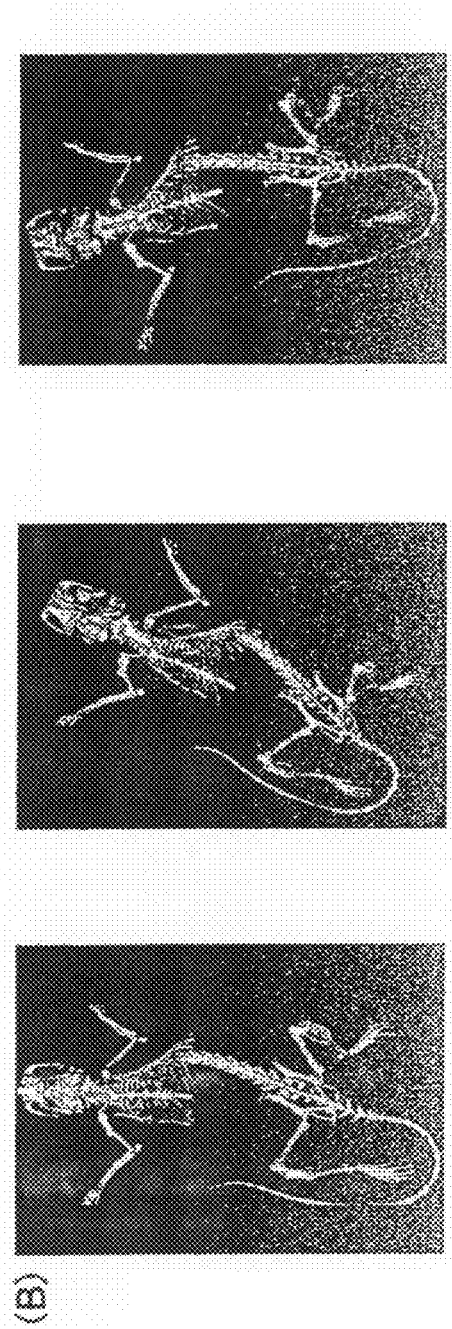

In Vivo Fluorescence Imaging:

Fluorescence imaging was carried out using IVIS 200 Imaging System (Xenogen) (for Cy5.5, [excitation, 640 nm; emission, 720 nm]; for Alexa Fluor 750, [excitation, 745 nm; emission, 800 nm]). 0.25 mg/ml Cy5.5-labeled antibody 3H3 (IgG) or 1.0 to 1.5 mg/ml Alexa Fluor 750-labeled antibody 3H3 was administered at 0.15 ml/head via the caudal vein to ApoE$^{-/-}$ mice fed a high fat diet, and after two to 24 hours under inhalation anesthesia, in vivo fluorescence was observed and photographed using IVIS 200. The ApoE$^{-/-}$ mice were observed after shaving, because their black hair absorbs fluorescence. First, the fluorescence was observed with reflected light, and then with transmitted light. Three-dimensional (3D) images of mice were generated and integrated with the light source information (FIG. 9A: a three-dimensional image by IVIS before integration). In the figure, red dots correspond to fluorescent signals from labels linked to 3H3. The denser red dots mean stronger fluorescence intensity, showing the localization of the imaging agent.

Ex Vivo Imaging:

After 3D CT analysis, the mice were euthanized, and the hearts were perfused with 10 ml of PBS. The hearts and aortae were excised and their reflection fluorescence images were obtained using IVIS 200.

CT Imaging:

CT imaging was performed using eXplore Locus CT System (GE Healthcare). Under inhalation anesthesia, the same mice used in the IVIS 200 imaging were irradiated with X ray to obtain CT images.

Integration of Fluorescence and CT Images:

Using general-purpose 3D visualization software (Amira; Mercury Computer Systems), fluorescent images detected by IVIS 200 were integrated with images obtained using CT (FIG. 9B: a three-dimensional CT image after integration).

Figure 8:
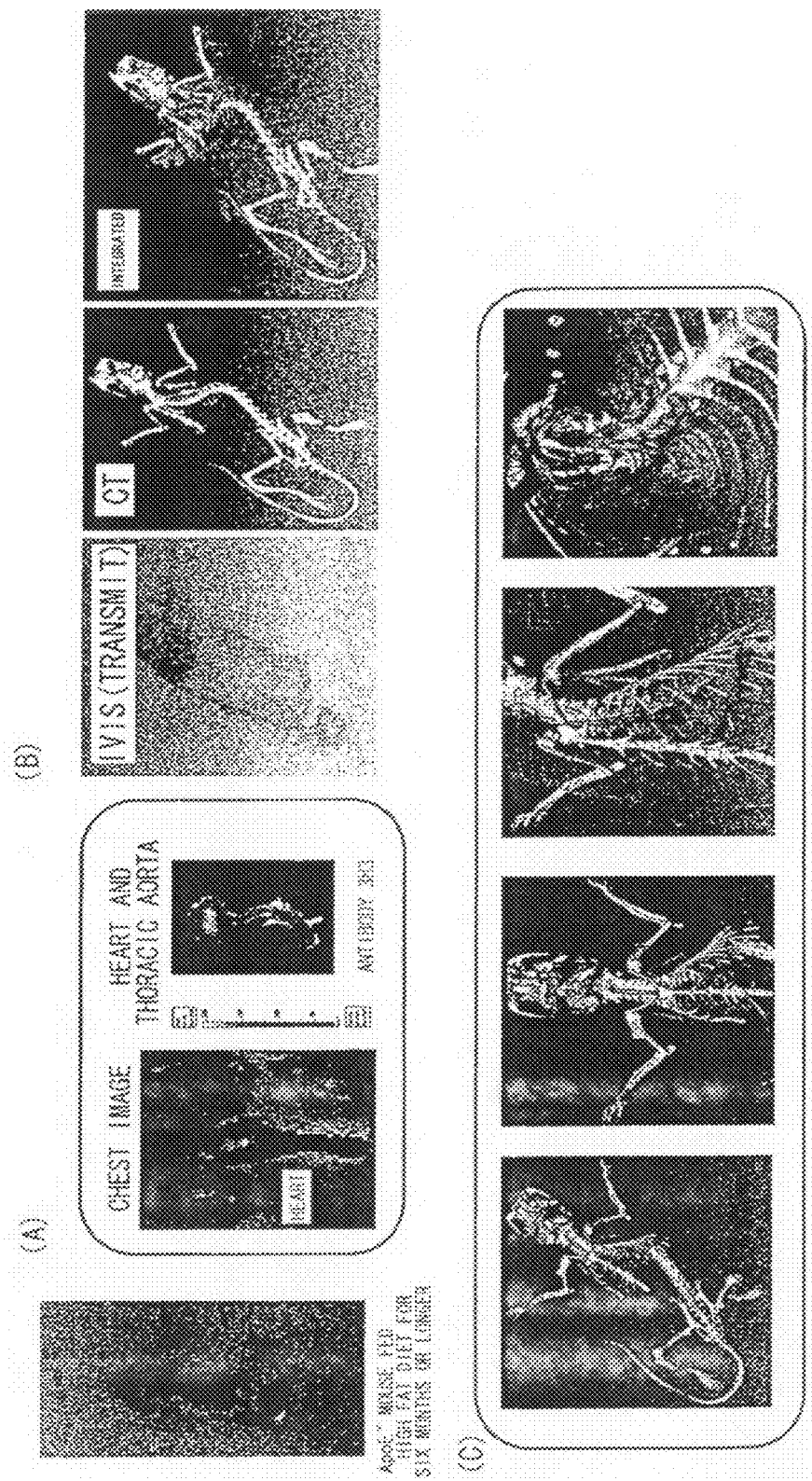
FIG. 8 is photographs showing three-dimensional imaging of arteriosclerosis using the specific antibody. (A), IVIS 200 fluorescence imaging using the specific antibody (reflection fluorescence microscopy); (B), IVIS 200 3D image obtained using transmitted light (left panel), CT 3D image before superimposing (middle panel), and the superimposed 3D image (right panel); (C) superimposed 3D images generated from IVIS fluorescence signal and 3D CT.

The procedure is shown schematically (FIG. 8).

(A) IVIS 200 fluorescence imaging using a specific antibody (reflection).

(B) IVIS 200 fluorescence image obtained using a specific antibody (transmitted light; left) and CT image (middle) before integration, and integrated image (right). In the fluorescence image (transmitted light; left), as the red dots become denser, the fluorescence intensity becomes stronger, suggesting that the imaging agent is localized and accumulated at the position (site that exhibits stronger binding reactivity to 3H3).

(C) Image resulting from integration of IVIS fluorescent signal and three-dimensional CT image: the photograph shows a three-dimensional image generated as animation in a computer-generated virtual space (three-dimensional graphic animation). The sites labeled were observed from multiple angles.

The visible light is absorbed by the body while the light of near-infrared wavelengths is hardly absorbed by the body. Thus, near-infrared fluorescent labels are suitable for in vivo imaging. In this experiment, antibodies labeled with Cy5.5 or Alexa Fluor 750 were administered to mice via the caudal vein, and the resulting fluorescence was monitored with IVIS 200 to assess the measurement conditions for the reflection and transmission fluorescence. When ApoE$^{-/-}$ mice with arteriosclerosis were observed by in vivo reflection fluorescence imaging using a Cy5.5-labeled antibody, intense signals were found in the aortic valve and thoracic aorta. Furthermore, by ex vivo imaging and ex vivo fluorescence microscopy, the fluorescently labeled antibody administered into the vein was demonstrated to be localized in arteriosclerotic plaques. However, when a Cy5.5-labeled antibody was used, the signal of transmission fluorescence was weak and thus it was difficult to identify the site of fluorescence in the three-dimensional (3D) images. By contrast, when an Alexa Fluor 750-labeled antibody was used, specific intense signals were observed two hours after intravenous administration in both reflection and transmission fluorescence images. In the generated three-dimensional image, intense fluorescent signals were recognized in the chest (FIGS. 8A and B, left panels). Then, the same mice were photographed by CT. The image (FIG. 8B, middle panel) resulting from extraction of bones and lungs from CT image was integrated with an IVIS 200 fluorescent image by Amira. The resulting integrated 3D image (FIG. 8B, right panel) showed that the presence of fluorescent signals in and around the heart. In the figure, the denser red dots suggest stronger fluorescence intensity, showing the localization of the imaging agent. CT image (middle panel) and 3D-CT integrated image (FIG. 8B, right panel) are shown. A three-dimensional image was generated as animation in a computer-generated virtual space (three-dimensional graphic animation). The sites labeled were observed from multiple angles (FIG. 8C).

The experimental result described above showed that when ApoE$^{-/-}$ mice with arteriosclerosis were observed by in vivo reflection fluorescence imaging using fluorescently labeled antibody 3H3, intense signals were found in the aortic valve and thoracic aorta. Furthermore, by ex vivo imaging and ex vivo fluorescence microscopy, the fluorescently labeled antibody administered into the vein was demonstrated to be localized in arteriosclerotic plaques.

The experiment described above demonstrated not only that arteriosclerosis in mice could be visualized by using a near-infrared fluorescent substance (Cy5.5 or Alexa 750)-labeled antibody, but also that the images could be integrated with three-dimensional CT images. Furthermore, it has been demonstrated that such antibodies enable detection of human arteriosclerotic plaques. The experimental results described herein will lead to clinically applicable technologies for diagnostic imaging. In addition, the mouse imaging techniques are already practicable as a screening system for drug discovery.

INDUSTRIAL APPLICABILITY

The sites (locations) of arteriosclerosis cannot be identified by conventional tests for arteriosclerosis. In contrast, the present invention provides non-invasive diagnostic methods that allow visual identification of the site and size of arteriosclerotic plaques (in particular, atheroma and atherosclerosis).

A screening system for therapeutic agents to treat atherosclerosis can be constructed by using arteriosclerosis-prone model mice (for example, apoE-deficient (ApoE−/−) mice; which maintain high plasma cholesterol level, and spontaneously develop an atherosclerosis-like condition) and antibodies for the imaging.

Furthermore, an imaging system for clinical diagnosis can be constructed by converting the antibodies into humanized antibodies. Thus, plaques or such detached from atheroma lesions of arteries are known to cause arterial embolism which leads to cerebral embolism or myocardial infarction. Methods for monitoring human arthrosclerosis which progresses insidiously, asymptomatically, and chronically can be expected to benefit strategies for preventing or treating lifestyle-related diseases.

The invention claimed is:

1. An isolated antibody that binds to a complex of oxidized LDL and $\beta_2$-glycoprotein I (oxidized LDL/$\beta_2$GPI complex) and comprises a pair of the heavy chain described in (a) or (b) below and the light chain described in (c) or (d) below:
   (a) an antibody comprising a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4;
   (b) an antibody comprising a heavy chain that comprises a heavy chain variable region having the amino acid sequence of SEQ ID NO: 1;
   (c) an antibody comprising a light chain that comprises CDR1 having the amino acid sequence of SEQ ID NO: 7, CDR2 having the amino acid sequence of SEQ ID NO: 8, and CDR3 having the amino acid sequence of SEQ ID NO: 9;
   (d) an antibody comprising a light chain that comprises a light chain variable region having the amino acid sequence of SEQ ID NO: 6.

2. An isolated antibody that binds to the same epitope as an antibody that binds to a complex of oxidized LDL and $\beta_2$-glycoprotein I (oxidized LDL/$\beta_2$GPI complex), and which comprises a pair of the heavy chain described in (a) or (b) below and the light chain described in (c) or (d) below:
   (a) an antibody comprising a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4;
   (b) an antibody comprising a heavy chain that comprises a heavy chain variable region having the amino acid sequence of SEQ ID NO: 1;
   (c) an antibody comprising a light chain that comprises CDR1 having the amino acid sequence of SEQ ID NO: 7, CDR2 having the amino acid sequence of SEQ ID NO: 8, and CDR3 having the amino acid sequence of SEQ ID NO: 9;
   (d) an antibody comprising a light chain that comprises a light chain variable region having the amino acid sequence of SEQ ID NO: 6.

3. The antibody of claim 1, which is a humanized or chimeric antibody.

4. An imaging kit for visualizing an arteriosclerosis site, which comprises the antibody of claim 1.

5. The antibody of claim 1 for use in an imaging method for visualizing an arteriosclerosis site.

6. An imaging method for visualizing an arteriosclerosis site, which comprises administering to a mammal an antibody of claim 1 or claim 2 linked to a labeling substance, wherein the antibody binds to a complex of oxidized LDL and $\beta_2$-glycoprotein I (oxidized LDL/$\beta_2$GPI complex), and detecting a signal from the labeling substance.

7. A method of screening for a candidate compound for a therapeutic agent for arteriosclerosis, which comprises the steps of:
   (a) administering a candidate compound to an arteriosclerosis model nonhuman animal administered with the antibody of claim 1 or claim 2;
   (b) carrying out imaging of an arteriosclerotic plaque in an arteriosclerosis model nonhuman animal administered with the candidate compound and in an arteriosclerosis model nonhuman animal not administered with the candidate compound;
   (c) comparing the size or location of an arteriosclerotic plaque between the arteriosclerosis model nonhuman animal administered with the candidate compound and the arteriosclerosis model nonhuman animal not administered with the candidate compound; and
   (d) selecting a candidate compound that reduces or eliminates an arteriosclerotic plaque in the arteriosclerosis model nonhuman animal administered with the candidate compound as compared to the arteriosclerosis model nonhuman animal not administered with the candidate compound.

8. An imaging agent for visualizing an arteriosclerosis site, which comprises an isolated antibody that binds to a complex of oxidized LDL and $\beta_2$-glycoprotein I (oxidized LDL/$\beta_2$GPI complex), and which comprises a pair of the heavy chain described in (a) or (b) below and the light chain described in (c) or (d) below:
- (a) an antibody comprising a heavy chain that comprises CDR1 having the amino acid sequence of SEQ ID NO: 2, CDR2 having the amino acid sequence of SEQ ID NO: 3, and CDR3 having the amino acid sequence of SEQ ID NO: 4;
- (b) an antibody comprising a heavy chain that comprises a heavy chain variable region having the amino acid sequence of SEQ ID NO: 1;
- (c) an antibody comprising a light chain that comprises CDR1 having the amino acid sequence of SEQ ID NO: 7, CDR2 having the amino acid sequence of SEQ ID NO: 8, and CDR3 having the amino acid sequence of SEQ ID NO: 9;
- (d) an antibody comprising a light chain that comprises a light chain variable region having the amino acid sequence of SEQ ID NO: 6.

9. The imaging agent of claim 8, which is an in vivo imaging agent.

10. The imaging agent of claim 8 for in vivo administration.

11. The imaging agent of claim 8 for determining the location and/or size of atheroma in arteriosclerosis.

* * * * *

UNITED STATES PATENT AND TRADEMARK OFFICE
CERTIFICATE OF CORRECTION

| | | |
|---|---|---|
| PATENT NO. | : 8,575,314 B2 | Page 1 of 1 |
| APPLICATION NO. | : 13/000319 | |
| DATED | : November 5, 2013 | |
| INVENTOR(S) | : Matsuura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 172 days.

Signed and Sealed this
Twenty-sixth Day of May, 2015

Michelle K. Lee
*Director of the United States Patent and Trademark Office*

```
                       SEQUENCE LISTING

<160> NUMBER OF SEQ ID NOS: 36

<210> SEQ ID NO 1
<211> LENGTH: 118
<212> TYPE: PRT
<213> ORGANISM: Mus musculus

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Ala Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
    50                  55                  60

Arg Gly Arg Phe Thr Ile Ser Arg Asp Asn Ala Lys Asn Thr Leu Tyr
65                  70                  75                  80

Leu Gln Met Cys Ser Leu Arg Ser Glu Asp Thr Ala Met Tyr Tyr Cys
                85                  90                  95

Ala Arg Phe Asp Gly Tyr Tyr Ala Met Asp Tyr Trp Gly Gln Gly Thr
            100                 105                 110

Ser Val Thr Val Ser Ser
        115

<210> SEQ ID NO 2
<211> LENGTH: 5
<212> TYPE: PRT
<213> ORGANISM: Mus musculus

<400> SEQUENCE: 2

Ser Tyr Ala Met Ser
1               5

<210> SEQ ID NO 3
<211> LENGTH: 17
<212> TYPE: PRT
<213> ORGANISM: Mus musculus

<400> SEQUENCE: 3
```

Thr Ile Ser Ser Gly Gly Ser Tyr Thr Tyr Tyr Pro Asp Ser Val Arg
1               5                   10                  15

Gly

<210> SEQ ID NO 4
<211> LENGTH: 9
<212> TYPE: PRT
<213> ORGANISM: Mus musculus

<400> SEQUENCE: 4

Phe Asp Gly Tyr Tyr Ala Met Asp Tyr
1               5

<210> SEQ ID NO 5
<211> LENGTH: 354
<212> TYPE: DNA
<213> ORGANISM: Mus musculus

<400> SEQUENCE: 5
gaagtgcagt tggtggagtc tgggggaggc ttagtgaagc ctggagggtc cctgaaactc      60
tcctgtgcag cctctggatt cactttcagt agctatgcca tgtcttgggc tcgccagact     120
ccggagaaga ggctggagtg ggtcgcaacc attagtagtg gtggtagtta cacctactat     180
ccagacagtg tgaggggtcg attcaccatc tccagagaca tgccaagaa cacccctgtac     240 ctgcaaatgt gcagtctgag gtctgaggac acggccatgt attactgtgc aaggtttgat     300
ggttactatg ctatggacta ctggggtcaa ggaacctcag tcaccgtctc ctca           354

<210> SEQ ID NO 6
<211> LENGTH: 107
<212> TYPE: PRT
<213> ORGANISM: Mus musculus

<400> SEQUENCE: 6

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ser Gly Thr Lys Leu Glu Ile Lys
            100                 105

<210> SEQ ID NO 7
<211> LENGTH: 11
<212> TYPE: PRT
<213> ORGANISM: Mus musculus

<400> SEQUENCE: 7

Lys Ala Ser Gln Asp Val Gly Ser Ala Val Ala
1               5                   10

<210> SEQ ID NO 8
<211> LENGTH: 7

```
<212> TYPE: PRT
<213> ORGANISM: Mus musculus

<400> SEQUENCE: 8

Trp Ala Ser Thr Arg His Thr
1               5

<210> SEQ ID NO 9
<211> LENGTH: 9
<212> TYPE: PRT
<213> ORGANISM: Mus musculus

<400> SEQUENCE: 9

Gln Gln Tyr Ser Ser Tyr Pro Leu Thr
1               5

<210> SEQ ID NO 10
<211> LENGTH: 321
<212> TYPE: DNA
<213> ORGANISM: Mus musculus

<400> SEQUENCE: 10
gacattgtga tgacccagtc tcacaaattc atgtccacat cagtcggaga cagggtcagc      60
atcacctgca aggccagtca ggatgtgggt tctgctgtag cctggtatca acagaaacca     120
gggcaatctc ctaaactact gatttactgg gcatccaccc ggcacactgg agtccctgat     180
cgcttcacag gcagtggatc tgggacagat ttcactctca ccattagcag tttgcagtct     240
gaagacttgg cagattattt ctgtcagcaa tatagcagct atcctctcac ggttcggctcg     300 gggacaaagt tggaaataaa a                                                321

<210> SEQ ID NO 11
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 11
atgaagttgc ctgttaggct gttggtgctg                                       30

<210> SEQ ID NO 12
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 12
atggagwcag acacactcct gytatgggtg                                       30

<210> SEQ ID NO 13
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 13
atgagtgtgc tcactcaggt cctggsgttg                                       30

<210> SEQ ID NO 14
<211> LENGTH: 33
<212> TYPE: DNA
<213> ORGANISM: Artificial
```

```
<220> FEATURE:
<223> OTHER INFORMATION: An artificially synthesized primer sequence

<400> SEQUENCE: 14
atgaggrccc ctgctcagwt tyttggmwtc ttg                            33

<210> SEQ ID NO 15
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 15
atggatttwc aggtgcagat twtcagcttc                               30

<210> SEQ ID NO 16
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 16
atgaggtkcy ytgytsagyt yctgrgg                                  27

<210> SEQ ID NO 17
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 17
atgggcwtca agatggagtc acakwyycwg g                             31

<210> SEQ ID NO 18
<211> LENGTH: 31
<212> TYPE: DNA
<213> ORGANISM: Artificial
<220> FEATURE:
<223> OTHER INFORMATION: An artificially synthesized primer sequence

<400> SEQUENCE: 18 atgtgggay ctktttycmm ttttcaatt g                               31

<210> SEQ ID NO 19
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 19
atggtrtccw casctcagtt ccttg                                    25

<210> SEQ ID NO 20
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 20
atgtatatat gtttgttgtc tatttct                                  27
```

```
<210> SEQ ID NO 21
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 21
atggaagccc cagctcagct tctcttcc                                          28

<210> SEQ ID NO 22
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 22
actggatggt gggaagatgg                                                   20

<210> SEQ ID NO 23
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 23
atgaaatgca gctggggcat sttcttc                                           27

<210> SEQ ID NO 24
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 24
atgggatgga gctrtatcat sytctt                                            26

<210> SEQ ID NO 25
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 25
atgaagwtgt ggttaaactg ggttttt                                           27

<210> SEQ ID NO 26
<211> LENGTH: 25
<212> TYPE: DNA
<213> ORGANISM: Artificial
<220> FEATURE:
<223> OTHER INFORMATION: An artificially synthesized primer sequence

<400> SEQUENCE: 26
atgractttg ggytcagctt grttt                                             25

<210> SEQ ID NO 27
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 27
```

```
atggactcca ggctcaattt agttttcctt                                    30
```

<210> SEQ ID NO 28
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 28

```
atggctgtcy trgsgctrct cttctgc                                       27
```

<210> SEQ ID NO 29
<211> LENGTH: 26
<212> TYPE: DNA
<213> ORGANISM: Artificial
<220> FEATURE:
<223> OTHER INFORMATION: An artificially synthesized primer sequence

<400> SEQUENCE: 29

```
atggratgga gckggrtctt tmtctt                                        26
```

<210> SEQ ID NO 30
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 30

```
atgagagtgc tgattctttt gtg                                           23
```

<210> SEQ ID NO 31
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 31

```
atggmttggg tgtggamctt gctattcctg                                    30
```

<210> SEQ ID NO 32
<211> LENGTH: 27
<212> TYPE: DNA
<213> ORGANISM: Artificial
<220> FEATURE:
<223> OTHER INFORMATION: An artificially synthesized primer sequence

<400> SEQUENCE: 32

```
atgggcagac ttacattctc attcctg                                       27
```

<210> SEQ ID NO 33
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 33

```
atggattttg ggctgatttt ttttattg                                      28
```

<210> SEQ ID NO 34
<211> LENGTH: 27
<212> TYPE: DNA
<213> ORGANISM: Artificial

-continued

```
<220> FEATURE:
<223> OTHER INFORMATION: An artificially synthesized primer sequence

<400> SEQUENCE: 34
atgatggtgt taagtcttct gtacctg                                           27

<210> SEQ ID NO 35
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 35
cagtggatag actgatgggg g                                                 21

<210> SEQ ID NO 36
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 36
cagtggatag acagatgggg g                                                 21
```